US010064890B2

(12) United States Patent
Sagi et al.

(10) Patent No.: US 10,064,890 B2
(45) Date of Patent: Sep. 4, 2018

(54) AMORPHOUS CALCIUM CARBONATE FOR THE TREATMENT OF CALCIUM MALABSORPTION AND METABOLIC BONE DISORDERS

(71) Applicant: AMORPHICAL LTD, Beer-Sheva (IL)

(72) Inventors: Amir Sagi, Omer (IL); Assaf Shechter, Tel Aviv (IL); Galit Shaltiel-Gold, Omer (IL); Michal Daniely, Ganey-Tiqwa (IL); Oren Meiron, Beer Sheva (IL)

(73) Assignee: AMORPHICAL LTD., Beer Sheva (IL)

( * ) Notice: Subject to any disclaimer, the term of this patent is extended or adjusted under 35 U.S.C. 154(b) by 95 days.

(21) Appl. No.: 14/364,992

(22) PCT Filed: Dec. 13, 2012

(86) PCT No.: PCT/IL2012/050521
§ 371 (c)(1),
(2) Date: Jun. 12, 2014

(87) PCT Pub. No.: WO2013/088440
PCT Pub. Date: Jun. 20, 2013

(65) Prior Publication Data
US 2015/0056306 A1 Feb. 26, 2015

Related U.S. Application Data

(60) Provisional application No. 61/680,721, filed on Aug. 8, 2012, provisional application No. 61/569,805, filed on Dec. 13, 2011.

(51) Int. Cl.
*A61K 33/10* (2006.01)
*A61K 31/663* (2006.01)
*A61K 35/612* (2015.01)

(52) U.S. Cl.
CPC ............ *A61K 33/10* (2013.01); *A61K 31/663* (2013.01); *A61K 35/612* (2013.01)

(58) Field of Classification Search
CPC ..... A61K 31/663; A61K 33/10; A61K 35/612
See application file for complete search history.

(56) References Cited

U.S. PATENT DOCUMENTS

2007/0041506 A1 2/2007 Bottino
2010/0096330 A1* 4/2010 Gotch ..................... A61K 31/00
210/647

FOREIGN PATENT DOCUMENTS

| CN | 101314031 | 12/2008 |
| CN | 102085356 | 6/2011 |
| GB | 2217988 | 11/1989 |
| JP | H01156985 | 6/1989 |
| JP | H10-236957 | 9/1998 |
| JP | 2003/292453 | 10/2003 |
| WO | 97/24069 | 7/1997 |
| WO | 98/57656 | 12/1998 |
| WO | 2005/115414 | 12/2005 |
| WO | 2007/048811 | 5/2007 |
| WO | 2008/041236 | 4/2008 |
| WO | 2009/053967 | 4/2009 |
| WO | 2009/087553 | 7/2009 |

OTHER PUBLICATIONS

Addadi et al., (2003) Taking advantage of disorder: amorphous calcium carbonate and its roles in biomineralization. Advanced Materials 15(12): 959-970.
Akamatsu, "Oriental Drugs, New Revision", 1st Ed. Ishiyaku Shuppan K. K., 1970, p. 911 English translation.
Akiva-Tal et al., (2011) In situ molecular NMR picture of bioavailable calcium stabilized as amorphous CaCO3 biomineral in crayfish gastroliths. Proc Natl Acad Sci USA 108(36): 14763-14768.
Bajpai et al., (2004) Pseudohypoparathyroidism Presenting with Bony Deformities Resembling Rickets. Indian Journal of Pediatrics 71(4): 345-347.
Cusano et al., (2012) Mini-review: new therapeutic options in hypoparathyroidism. Endocrine 41(3): 410-4.
Database Uniprot P98157 (1996).
Fong and Khan (2012) Hypocalcemia: updates in diagnosis and management for primary care. Can Fam Physician 58(2): 158-62.
Fujita (1990) Osteoporosis drugs. Chiryo 72: 455-459 English translation.
Gueguen et al., (2000) The bioavailability of dietary calcium. J Am Coll Nutr 19(suppl 2): 119S-136S.
Hu et al., (2004) Effect of calcium supplements on osteoporosis by using nuclear analytical techniques. J Radioanalytical & Nuclear Chemistry 259: 369-373.
Hu et al., (2010) Strongly bound citrate stabilizes the apatite nanocrystals in bone. Proc Natl Acad Sci USA 107(52): 22425-22429.
Johnsson et al., (1991) Adsorption and mineralization effects of citrate and phosphocitrate on hydroxyapatite. Calcif Tissue Int 49(2): 134-137.
Maruyama et al., (2011) Synthesizing a composite material of amorphous calcium carbonate and aspartic acid. Materials Letters 65(2): 179-181.
OsteoPhase. Tango advanced Nutrition—Healthy Bone Support Formula 2011.
Osteoporosis: How to strengthen your bones and prevent fractures. The healthier Life. 2005.
Raz et al., (2002) Stable amorphous calcium carbonate is the main component of the calcium storage structures of the crustacean Orchestia cavimana. Biol Bull 203: 269-274.
Reddi et al., (1980) Influence of phosphocitrate, a potent inhibitor of hydroxyapatite crystal growth, on mineralization of cartilage and bone. Biochem Biophys Res Commun 97(1): 154-159.

(Continued)

*Primary Examiner* — Snigdha Maewall
(74) *Attorney, Agent, or Firm* — Dorsey & Whitney LLP

(57) ABSTRACT

Provided are methods for treating calcium malabsorption and conditions associated with calcium malabsorption, employing the administration of a composition containing stable amorphous calcium carbonate. Further provided are methods for increasing bone mineral density in a bone metabolism associated disorders, diseases or conditions, employing the administration of said composition in combination with a bone resorption inhibitor.

19 Claims, 11 Drawing Sheets

(56) References Cited

OTHER PUBLICATIONS

Schneiders et al., (2007) Effect of modification of hydroxyapatite/collagen composites with sodium citrate, phosphoserine, phosphoserine/RGD-peptide and calcium carbonate on bone remodelling. Bone 40(4): 1048-1059.
Shechter et al., (2008) A gastrolith protein serving a dual role in the formation of an amorphous mineral containing extracellular matrix. Proc Natl Acad Sci U S A 105(20): 7129-7134.
Sipponen and Harkonen (2010) Hypochlorhydric stomach: a risk condition for calcium malabsorption and osteoporosis? Scand J Gastroenterol 45(2): 133-8.
Straub (2007) Calcium supplementation in clinical practice: a review of forms, doses, and indications. Nutr Clin Pract 22(3): 286-96.
Withnall (2000) Biology of Yabbies (cherax destructor). Aquaculture Information Notes, Department of Primary Industries, 6 pages.
Bentov et al., (2010) Stabilization of amorphous calcium carbonate by phosphate rich organic matrix proteins and by single phosphoamino acids. J Struct Biol 171(2): 207-15.
Meiron et al., (2011) Solubility and bioavailability of stabilized amorphous calcium carbonate. J Bone Miner Res 26(2): 364-72.
Bonjour, P. et al., "Who Scientific Group on the Assessment of Osteoporosis at Primary Health Care Level", WHO Summary Meeting Report, Brussels, Belgium, pp. 1-13, May 5-7, 2004.
Beers, M. et al., "Osteoporosis", The Merck Manual of Diagnosis and Therapy, Seventeeth Edition, Sect. 5, Chap. 57, pp. 469-471, (1999).
Mayo Clinic Internal Medicine Board Review (Mayo Clinic Scientific Press). Edited by Ghosh AK. 9th Edition. Oxford University Press; Aug. 30, 2010; pp. 201-202.
Nakatsuji et al., (2000) Changes in the Amounts of the Molt-Inhibiting Hormone in Sinus Glands during the Molt Cycle of the American Crayfish, *Procambarus clarkii*. Zoolog Sci 17(8): 1129-36.
Kanis, J.A., et al. "Osteoporosis International With Other Metabolic Bone Diseases," World Congress on Osteoporosis, Osteoarthritis and Musculoskeletal Diseases, vol. 27, Supplement 1, Apr. 14-17, 2016, pp. 1-2.
Chinese Medical Encyclopedia Endocrinology and Metabolism. Zhong Xueli, Shanghai Science and Technology Press, 1992, 1st Edition, pp. 67-68. Partial translation.
Drug Interactions—Principles and Biochemical Foundations, edited by Zhou Weishu et al., Science Press, 1990, 1st dition, pp. 80-81, Partial translation.

* cited by examiner

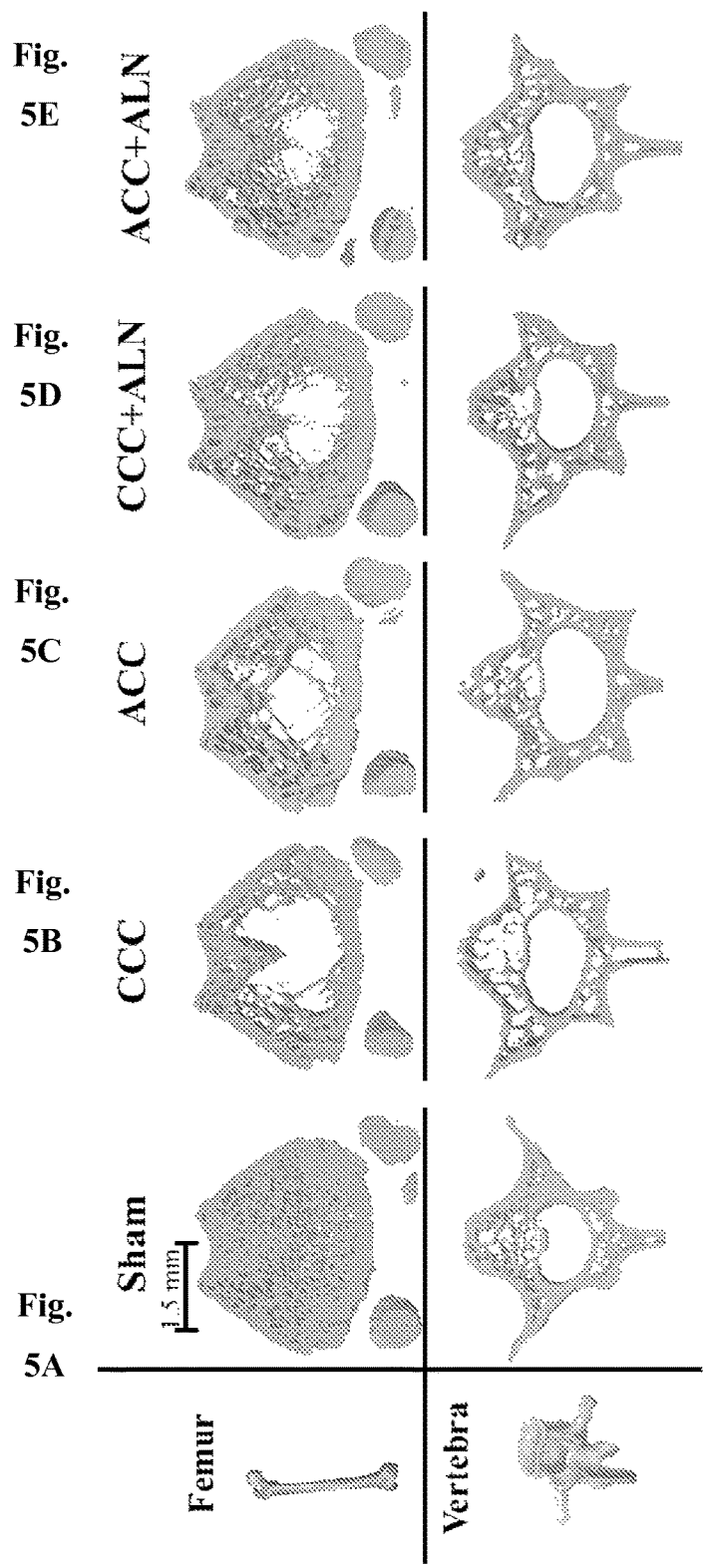

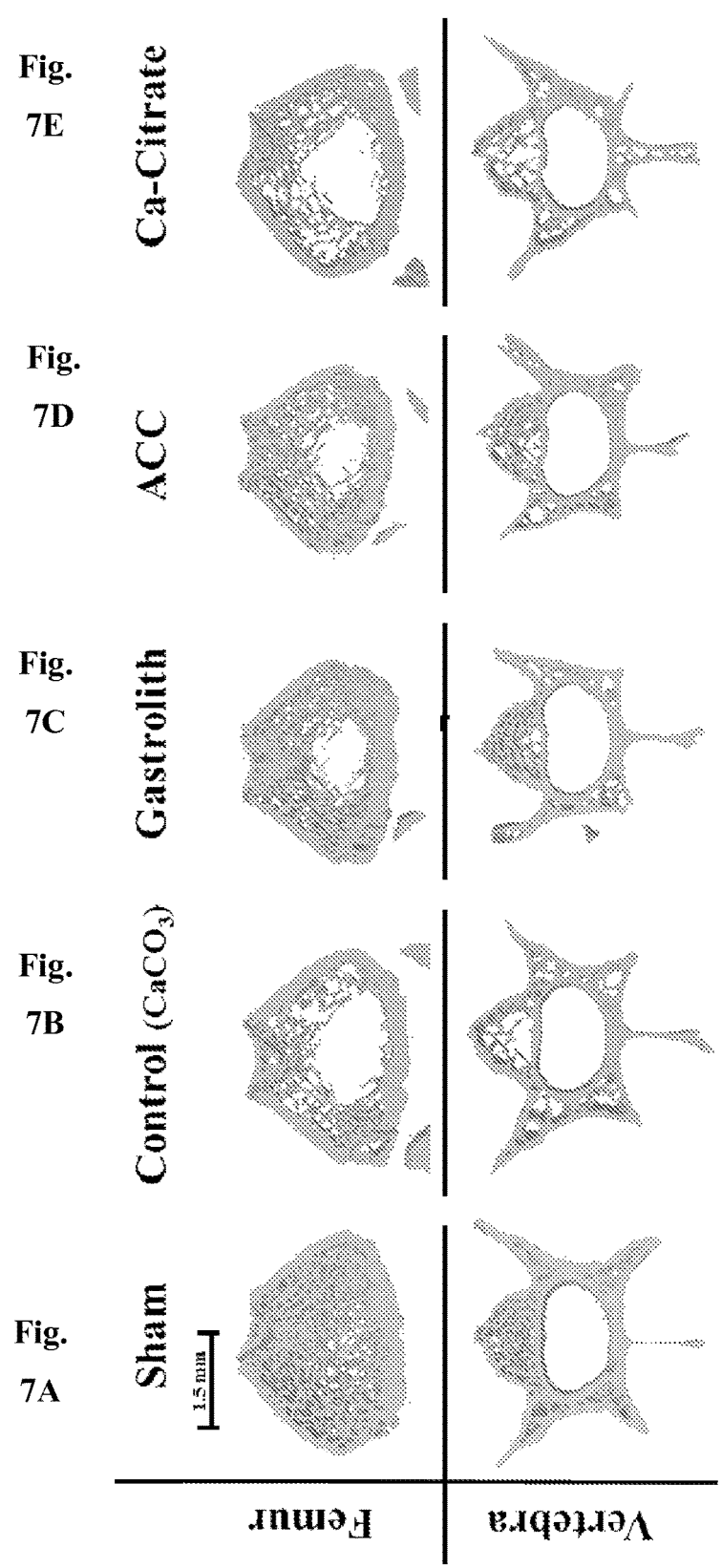

AMORPHOUS CALCIUM CARBONATE FOR THE TREATMENT OF CALCIUM MALABSORPTION AND METABOLIC BONE DISORDERS

FIELD OF THE INVENTION

The present invention relates to natural and synthetic amorphous calcium carbonate compositions for use in treatment of calcium malabsorption, and malabsorption associated disorders, diseases and conditions, and for increasing bone mineral density in calcium malabsorption and bone metabolism associated disorders.

BACKGROUND

Calcium is considered to be one of the most important minerals in the human body. It is required for maintaining bone mineral density, is essential for exocytosis of neurotransmitters, takes part in the contraction of muscle cells, replaces sodium as the depolarizing mineral in the heart, and participates in many other physiological functions. Calcium gastrointestinal absorption depends not only on the dietary calcium availability but on the absorptive capacity of the intestines, which is affected by physiological factors such as calcium reserves, hormonal regulation or previous dietary calcium supply. Dissolution of calcium salts (e.g. calcium carbonate) in the stomach is one step in the proper active and passive absorption of calcium as a calcium ion ($Ca^{(2+)}$) in the proximal small intestine. Stomach acid markedly increases dissolution and ionization of poorly soluble calcium salts. If acid is not properly secreted, calcium salts are minimally dissolved (ionized) and, subsequently, may not be properly and effectively absorbed. Atrophic gastritis, gastric surgery, and high-dose, long-term use of antisecretory drugs markedly reduce acid secretion and may, therefore, be risk conditions for malabsorption of dietary and supplementary calcium, and may thereby increase the risk of osteoporosis in the long term (Sipponen et al., Scand J. Gastroenterol. 2010; 45(2):133-8).

Calcium gastrointestinal absorption may also be decreased in patients after bariatric surgery, patients suffering from hypoparathyroidism, Crohn's disease, cystic fibrosis, inflammatory bowel disease or celiac disease. Individuals, consuming additional types of drugs, such as proton pump inhibitors, anticonvulsants, and chronic corticosteroids, may also develop calcium malabsorption.

Bioavailability of calcium depends on its gastrointestinal absorption and the incorporation of absorbed calcium into bone. As for intestinal absorption, physiological factors, particularly hormones, play a major role in the incorporation of calcium into bone. The bioavailability of calcium may therefore be defined as the fraction of dietary calcium that is potentially absorbable by the intestine and can be used for physiological functions, particularly bone mineralization, or to limit bone loss (Gueguen et al, Am Coll Nutr, 2000 vol. 19 no. suppl 2 119S-136S).

Bone mineral density loss is associated with various metabolic bone diseases, such as: osteopenia, osteomalacia, Rickets, osteitis fibrosa cystica, and osteoporosis. Studies have shown that inadequate intake of dietary calcium can induce many bone-related diseases, such as osteoporosis.

A standard medication for prevention and treatment of certain types of bone loss (including osteoporosis) is an anti-resorptive agent. One non-limiting example for the anti-resorptive agents are bisphosphonates, e.g. the bisphosphonate Alendronate (ALN). Administration of ALN attenuates the decline in bone mineral density (BMD), as ALN has a bone resorption inhibiting effect. However, it is an acknowledged problem that ALN also suppresses bone formation and its administration is associated with a risk of adverse symptoms. Use of several drugs in combination has been suggested for the improvement of patients' compliance and the therapeutic effect.

The calcium used in supplements today, whether obtained from natural sources or synthetic precipitates, may comprise both organic and inorganic calcium salts. In specific conditions where calcium gastrointestinal absorption is limited, standard intake of the available supplements is insufficient to promote absorption, resulting in a need to increase intake doses. The requirement of consumption of higher calcium doses in malabsorption-associated conditions leads to adverse effects like constipation, kidney stones, vascular problems and subsequent reduced compliance. Moreover, most calcium supplements require low gastric pH in order to be efficiently dissolved and absorbed through the gut, and thus their bioavailability is superior in a fasting state.

Over the past 20 years, a rapidly growing scientific interest in the thermodynamically unstable amorphous polymorph of calcium carbonate, named amorphous calcium carbonate (ACC), has emerged. In nature, ACC is utilized by a small number of organisms, mainly crustaceans and other invertebrates that developed capabilities for stabilizing ACC in transient mineral deposition sites. These organisms require an exceptional efficient mineral source for the periodical mobilization, absorption and precipitation of calcium. In some crustaceans, such as the freshwater crayfish, ACC is stored in large quantities in specialized transient storage organs, named the Gastrolith.

In recent years, some of the inventors of the present invention have disclosed use of the gastrolith organs, ground to a fine powder useful as pharmaceutical and nutraceutical calcium compositions (WO 05/115414). It was disclosed that daily oral consumption of compositions comprising gastrolith components dramatically improves a range of conditions such as bone disorders, bone fractures, and cancer (WO 2008/041236). Pharmaceutical and nutraceutical compositions comprising ACC and phosphorylated peptides or amino acids for treating various disorders and conditions are disclosed in WO 2009/053967.

There is an unmet need for efficient treatment of calcium malabsorption, calcium malabsorption associated bone density loss and bone metabolism associated diseases.

SUMMARY OF THE INVENTION

The present invention provides a method of use of a composition comprising synthetic or natural stable ACC for treatment of calcium malabsorption. It is disclosed herein for the first time that ACC can overcome the deficiencies of other types of calcium supplements even in patients suffering from calcium malabsorption.

The treatment of calcium malabsorption may furthermore prevent or decrease or delay the onset of calcium deficiency related disorders, diseases. According to some embodiments conditions related to calcium deficiency include patients after bariatric or gastric surgery, patients suffering from hypoparathyroidism, vitamin D deficiency, renal tubular diseases, renal failure, pancreatitis, hypoproteinemia, and hyperphosphatemia. According to alternative embodiments diseases involving calcium malabsorption include Crohn's disease, cystic fibrosis, inflammatory bowel disease, celiac disease, and atopic gastritis. According to further embodiments calcium malabsorption may encompass subjects with enhanced bone formation and individuals consuming corticosteroids, proton pump inhibitors, anticonvulsants, rifampin and similar antibiotics, chelating agents, and antisecretory drugs.

Enhanced calcium gastrointestinal absorption of stable ACC compared to other calcium supplements may delay or minimize conditions and disorders resulting from calcium deficiency in other populations including postmenopausal women, and perimenopausal women, elderly men, children, adolescents, pregnant women, and breastfeeding women.

Enhanced calcium bioavailability of ACC may further delay or minimize bone density loss in subjects suffering from calcium malabsorption. The present invention provides use of a composition comprising synthetic or natural stable ACC for increasing the bone mineral density in a subject in metabolic bone disorders, diseases and conditions. The composition of the present invention is further used for delaying the onset and for treatment of said disorders, diseases or conditions, comprising osteomalacia, Paget's disease of bone, osteopenia, osteitis fibrosa cystica, Rickets, osteoporosis and acute alcohol consumption In one aspect, the invention provides a method of treating calcium malabsorption in a subject in need of such treatment, comprising administering to said subject an effective amount of stable amorphous calcium carbonate (ACC) comprising at least one stabilizer. According to some embodiments ACC is of synthetic origin. According to other embodiments ACC is of natural origin.

According to some embodiments the stabilizer is selected from the group consisting of organic acids, phosphoric or sulfuric esters of hydroxy carboxylic acids, hydroxyl bearing organic compounds, and combinations thereof. Each possibility represents a separate embodiment of the invention. In some embodiments, said stabilizer comprises at least one component selected from phosphoric or sulfuric esters of hydroxylcarboxylic acids and hydroxyl bearing organic compounds. In some embodiments, said stabilizer comprises at least one component selected from phosphorylated amino acids and polyols. Said amino acids may be present in amino acid derivatives or oligopeptides or polypeptides, and said polyols may comprise alcohols or saccharides. Each possibility represents a separate embodiment of the invention. According to some embodiments the phosphorylated amino acids are selected from phosphoserine and phospho-threonine. According to some embodiments, said stabilizer comprises at least one saccharide selected from mono-, di-, oligo-, and polysaccharides.

According to some embodiments, said stabilizer comprises hydroxyl bearing organic compounds further combined with at least one alkali hydroxide. According to some embodiments, the stabilizer is a carboxylic acid, preferably citric acid, tartaric acid or malic acid. In some embodiments, said stabilizer comprises at least one compound selected from phosphorylated amino acids, phosphorylated peptides, chitin with at least one peptide, and polyol with alkaline hydroxide. According to some exemplary embodiments, said ACC is obtained from isolated crustacean gastroliths. According to one embodiment, said natural ACC is stabilized by chitin and polypeptides. According to another embodiment, the ACC is synthetic, wherein said synthetic ACC is stabilized by phosphorylated amino acids selected from phosphoserine or phosphothreonine. According to another embodiment said synthetic ACC is stabilized by phosphoserine in combination with citric acid. According to still another embodiment, said synthetic ACC is stabilized by citric acid. According to yet another embodiment, said ACC is stabilized by sucrose in combination with sodium hydroxide.

According to some embodiments, the subject suffers from a disorder of calcium metabolism associated with a decrease of plasma calcium concentration below 8.8 mg/dL. According to some embodiments, the subject in need of the treatment is selected from the group consisting of patients suffering from hypoparathyroidism, vitamin D deficiency, renal tubular diseases, renal failure, pancreatitis, hypoproteinemia, Crohn's disease, cystic fibrosis, inflammatory bowel disease, celiac disease, hyperphosphatemia, atopic gastritis, patients after bariatric or gastric surgery, subjects with enhanced bone formation, and subjects obtaining medicaments selected from corticosteroids, proton pump inhibitors, anticonvulsants, rifampin and similar antibiotics, chelating agents, and antisecretory drugs. According to some embodiments, the subject is selected from postmenopausal or perimenopausal women. According to some embodiments said subject is susceptible to the development of bone mineral density loss associated disorders, diseases and conditions. The bone density loss associated disorder in a subject in a need of calcium malabsorption treatment, may be osteoporosis.

In another embodiment, the invention provides a pharmaceutical composition comprising stable amorphous calcium carbonate (ACC) comprising at least one stabilizer selected from the group consisting of organic acids, phosphoric or sulfuric esters of hydroxy carboxylic acids, and hydroxyl bearing organic compounds, for use in treating calcium malabsorption. The pharmaceutical composition according to the invention may further comprise carriers, adjuvants, diluents, or excipients.

In another embodiment, the invention is directed to the use of amorphous calcium carbonate, comprising at least one stabilizer selected from the group consisting of organic acids, phosphoric or sulfuric esters of hydroxy carboxylic acids, and hydroxyl bearing organic compounds for treating calcium malabsorption.

In another embodiment, the invention is directed to the use of amorphous calcium carbonate, comprising at least one stabilizer selected from the group consisting of organic acids, phosphoric or sulfuric esters of hydroxy carboxylic acids, and hydroxyl bearing organic compounds in the preparation of a medicament for treating calcium malabsorption.

In another aspect, the invention relates to a composition comprising stable amorphous calcium carbonate (ACC) comprising at least one stabilizer for the treatment of calcium malabsorption associated disorders, diseases and conditions.

The invention further encompasses the use of a composition comprising stable amorphous calcium carbonate (ACC) in the preparation of a medicament for treatment (in fed or fasting state) of calcium malabsorption in calcium malabsorption associated disorders, diseases and conditions, wherein the ACC is finely mixed with at least one stabilizer. In one embodiment composition comprising stable ACC has a superior gastrointestinal absorption when administered in a fed state. In another embodiment composition comprising stable ACC has a superior gastrointestinal absorption when administered in a fasting state.

In another aspect, the invention provides a method for the enhancement of bone mineral density in a bone metabolism associated disorder, disease or condition, comprising administering an effective amount of a composition comprising stable amorphous calcium carbonate (ACC) and at least one stabilizer to a mammalian subject. According to some embodiments ACC is of synthetic origin. According to other embodiments ACC is of natural origin. According to some embodiments, the stabilizer is selected from the group consisting of organic acids, phosphoric or sulfuric esters of hydroxy carboxylic acids, hydroxyl bearing organic compounds, and combinations thereof. Each possibility represents a separate embodiment of the invention. In some embodiments, said stabilizer comprises at least one component selected from phosphoric or sulfuric esters of hydroxylcarboxylic acids and hydroxyl bearing organic compounds. In some embodiments, said stabilizer comprises at least one component selected from phosphorylated amino acids and polyols. Said amino acids may be present in amino acid derivatives or oligopeptides or polypeptides, and said polyols may comprise alcohols or saccharides. Each possibility represents a separate embodiment of the invention. According to some embodiments, the phosphorylated amino acids are selected from phosphoserine and phosphothreonine. According to some embodiments, said stabilizer comprises at least one saccharide selected from mono-, di-, oligo-, and polysaccharides.

According to some embodiments, said stabilizer comprises hydroxyl bearing organic compounds further combined with at least one alkali hydroxide. According to some embodiments, the stabilizer is a carboxylic acid, preferably citric acid, tartaric acid or malic acid. In some embodiments, said stabilizer comprises at least one compound selected from phosphorylated amino acids, phosphorylated peptides, chitin with at least one peptide, and polyol with alkaline hydroxide. According to some embodiments, said ACC is obtained from isolated crustacean gastrolith.

According to some embodiments, the method for the enhancement of bone mineral density comprises administration of the composition comprising stable ACC in combination with a bone resorption inhibitor. According to some embodiments, the bone resorption inhibitor is bisphosphonate. According to some embodiments, the bisphosphonate is selected from Alendronate, Risedronate, Tiludronate, Ibandronate, Zolendronate, Pamidronate, Etidronate, and salts and esters thereof. According to one embodiment, the bisphosphonate is Alendronate. In some embodiments, the composition is administered in combination with lower therapeutic doses of bisphosphonate Alendronate, compared to the dose required without calcium supplements or with calcium supplements other than stable ACC supplements. According to some embodiments, the invention provides a method for the enhancement of bone mineral density in bone metabolism associated disorders, diseases or conditions, selected from osteoporosis, oseomalacia, Paget's disease of bone, osteopenia, osteitis fibrosa cystica and Rickets. In one specific embodiment, the invention provides a method for enhancing bone mineral density in osteoporosis. According to some embodiments, the invention provides a method for the enhancement of bone mineral density in bone metabolism associated disorders, diseases or conditions, selected from osteomalacia, Paget's disease of bone, osteopenia, osteitis fibrosa cystica, Rickets, osteoporosis and acute alcohol consumption, comprising administration of said composition in combination with bone resorption inhibitor. In one specific embodiment, the invention provides a method for enhancing bone mineral density in osteoporosis, comprising administration of said composition in combination with bisphosphonate Alendronate. According to the method of the present invention, the composition is administered to a mammalian subject selected from postmenopausal women, elderly men, children, adolescents, pregnant women, and breastfeeding women. According to some embodiments, the method for the enhancement of bone mineral density comprises administration of the composition comprising stable ACC, wherein said subject is selected from patients suffering from calcium malabsorption and calcium malabsorption associated disorders, diseases and conditions.

The invention further provides the use of a composition comprising stable amorphous calcium carbonate (ACC) comprising at least one stabilizer, selected from the group consisting of organic acids, phosphoric or sulfuric esters of hydroxy carboxylic acids, and hydroxyl bearing organic compounds for use in the preparation of a medicament for the enhancement of bone mineral density in a bone metabolism associated disorder, disease or condition The pharmaceutical composition according to the invention may further comprise carriers, adjuvants, diluents, or excipients.

In still another aspect, the invention provides a method of enhancing calcium gastrointestinal absorption in a subject suffering from calcium malabsorption, comprising administering to said subject an effective amount of ACC comprising at least one stabilizer. According to some embodiments, the administration is performed to said subject selected from a subject in a fasting state and in a fed state.

All the above and other characteristics and advantages of the invention will be further understood through the following illustrative and non-limitative description of embodiments thereof, with reference to the appended drawings.

BRIEF DESCRIPTION OF THE DRAWINGS

FIGS. 5A-5E: Three-dimensional reconstruction of a representative distal femurs and 4th vertebras cross sections from each treatment group.

Tubercular bone region for Sham (FIG. 5A); Crystalline calcium carbonate (CCC) (FIG. 5B); amorphous calcium carbonate (ACC) (FIG. 5C); CCC+alendronate (ALN) (FIG. 5D); and ACC+ALN (FIG. 5E). Scale bar represents 1.5 mm distance.

FIGS. 6A-6D: Trabecular bone mineral density (Tb.BMD) and bone volume from total bone tissue volume (BV/TV) of the groups obtained by μCT.

Figure 6A:
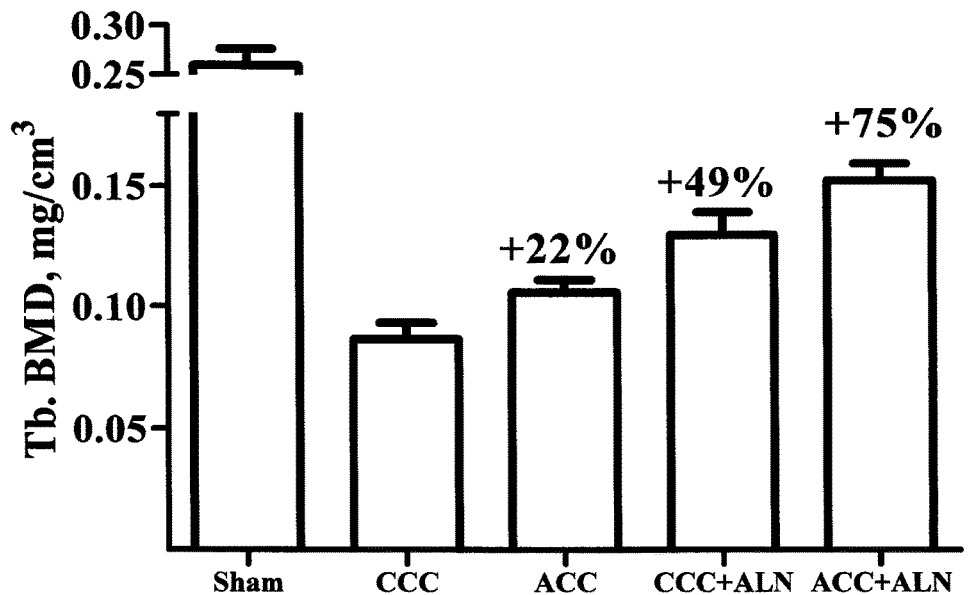

FIG. 6A: Tb.BMD of the distal femur.

Figure 6B:
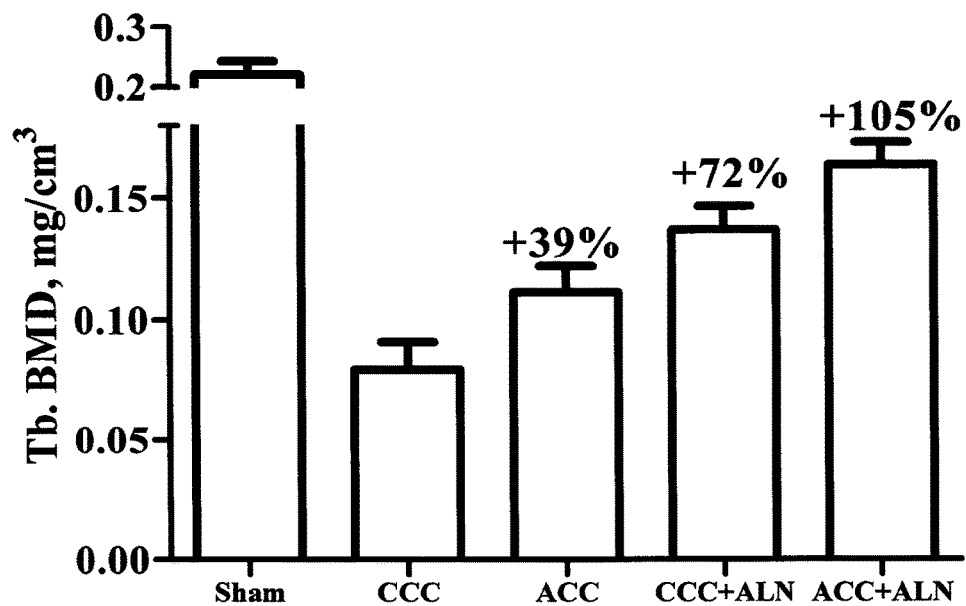

FIG. 6B: Tb.BMD of the 4th lumbar vertebra.

Figure 6C:
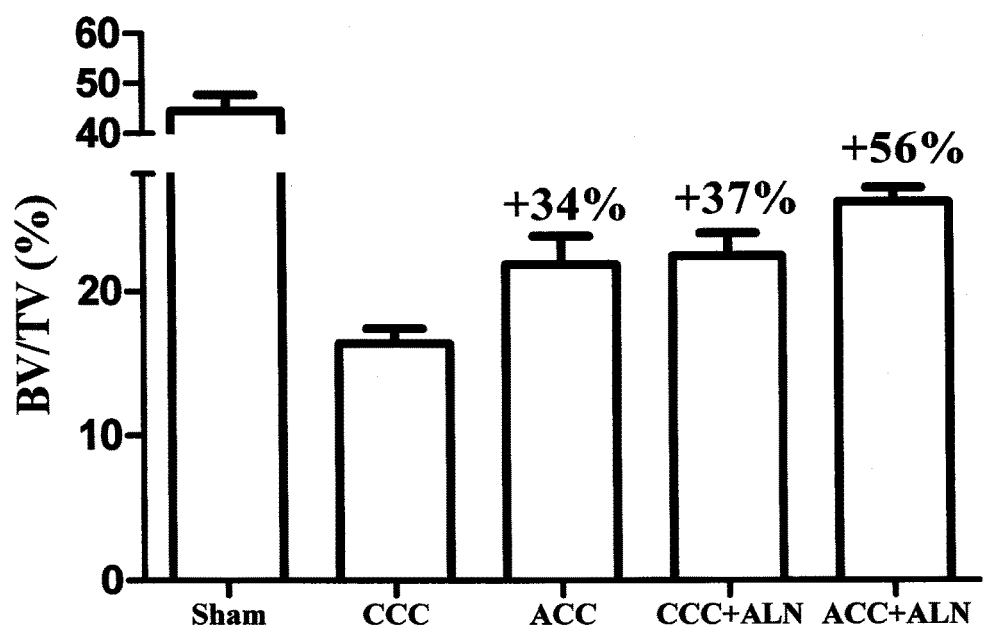

FIG. 6C: BV/TV of the distal femur.

Figure 6D:
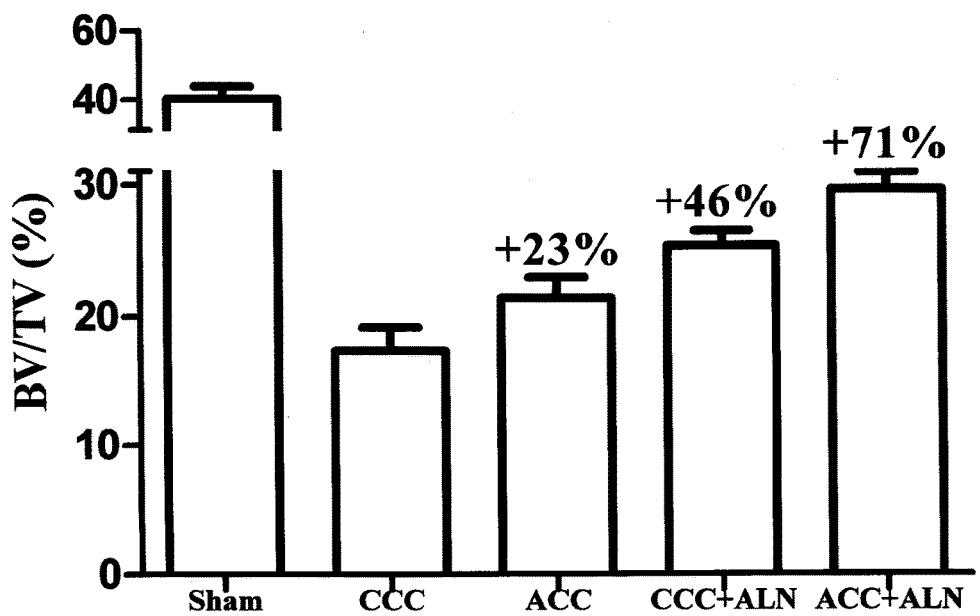

FIG. 6D: BV/TV of the 4th lumbar vertebra.

Percentage represent increase from CCC treated group (control).

FIGS. 7A-7E: Three-dimensional reconstruction of a representative distal femurs and 4th vertebras cross sections from each treatment group.

Tubercular bone region for sham (FIG. 7A); control (FIG. 7B); gastrolith (Gast) (FIG. 7C); amorphous calcium carbonate (ACC) (FIG. 7D); and citrate (FIG. 7E). Scale bar represents 1.5 mm distance.

Figure 8A:
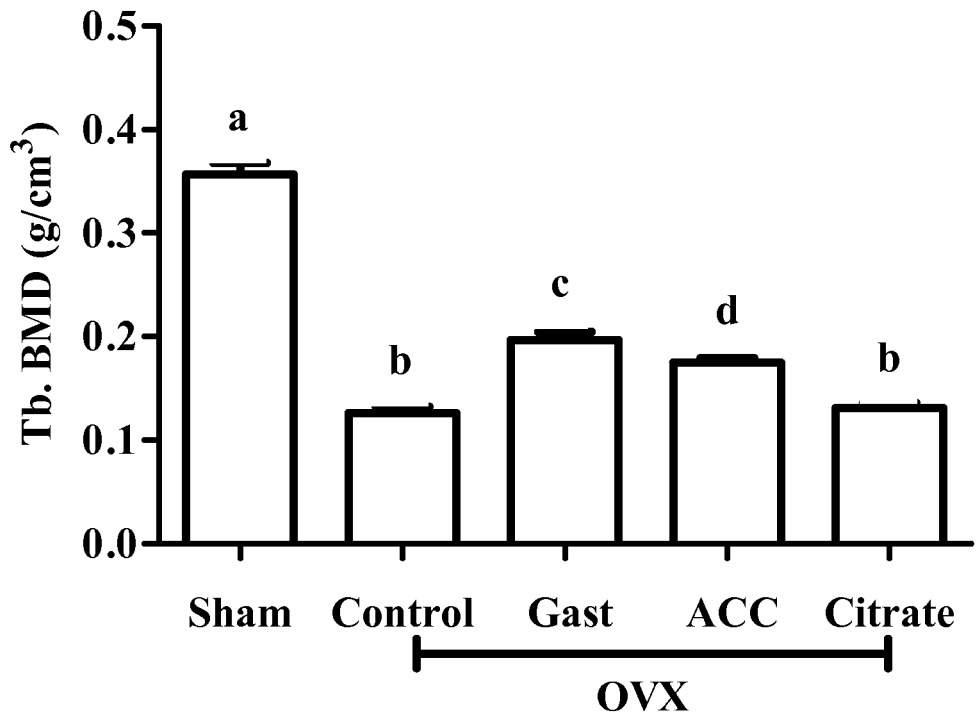
Figure 8B:
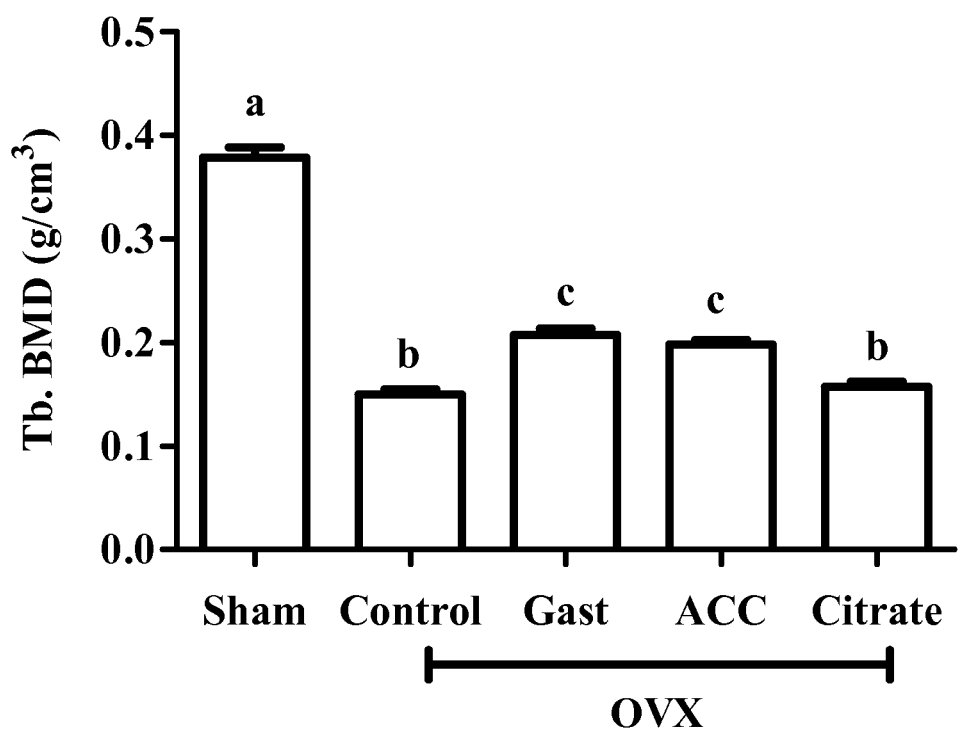

FIGS. 8A-8B: Trabecular bone mineral density (Tr.BMD) of the groups obtained by μCT.

FIG. 8A: Tr.BMD of the distal femurs.

FIG. 8B: Tr.BMD of the $4^{th}$ lumbar vertebras.

One-way ANOVA: $p<0.001$. Letters represent Fishers LSD post-hoc comparison.

Figure 9A:
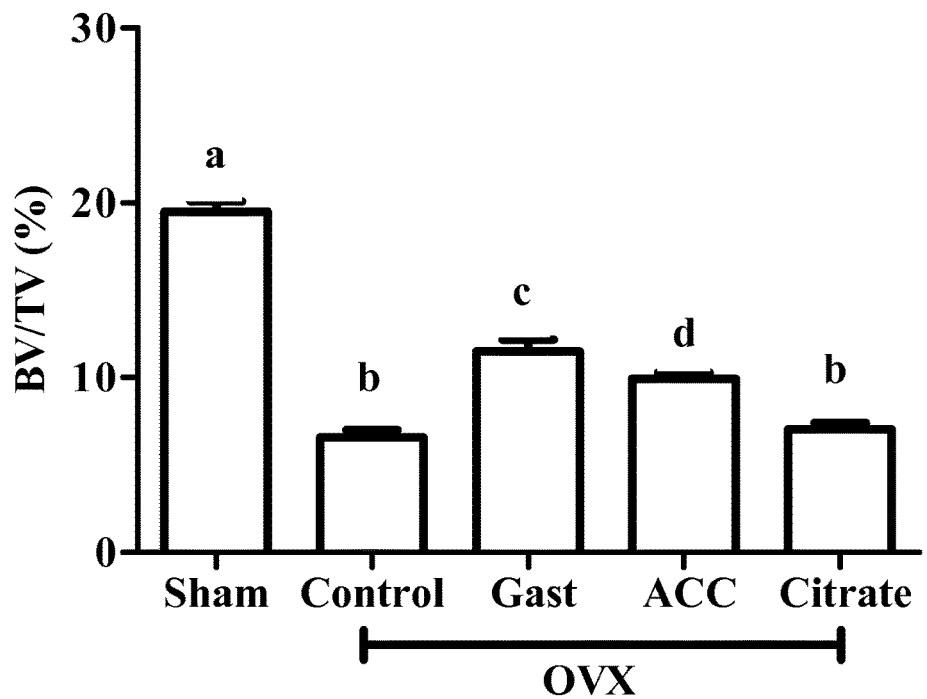
Figure 9B:
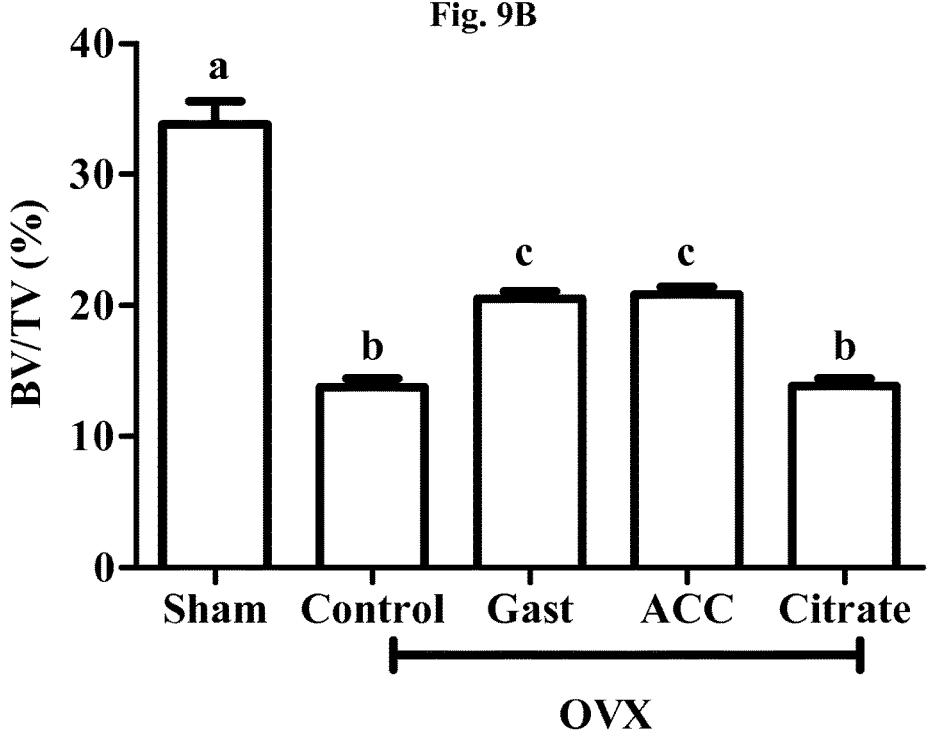

FIGS. 9A-9B: Trabecular bone volume from total bone tissue (BV/TV) of the treatment groups obtained by μCT.

FIG. 9A: BV/TV of the distal femurs.

FIG. 9B: BV/TV of the $4^{th}$ lumbar vertebras.

One-way ANOVA: $p<0.001$. Letters represent Fishers LSD post-hoc comparison.

FIGS. 10A-10G: Mechanical microarchitectural properties of the lumbar vertebras.

Figure 10A:
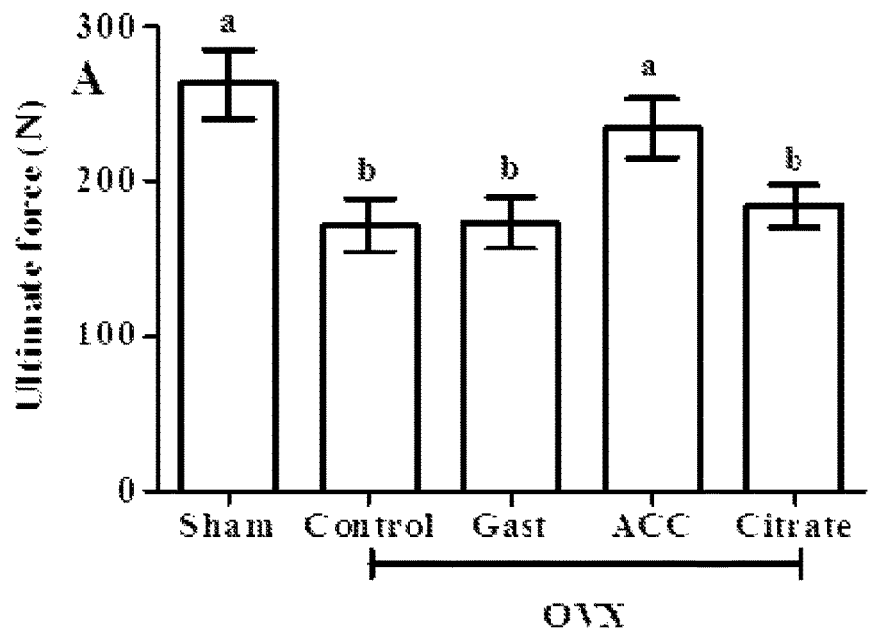
Figure 10B:
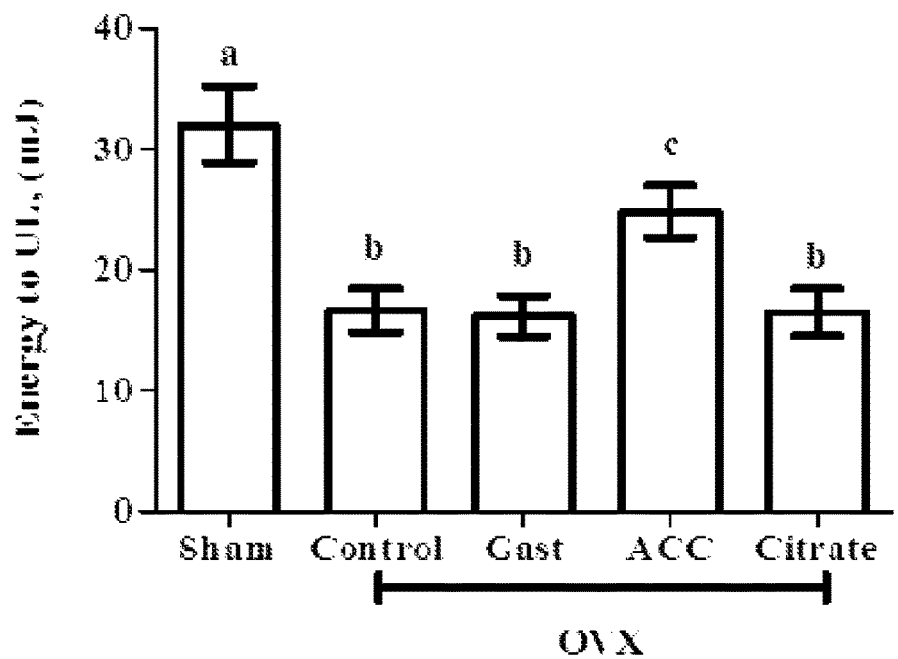
Figure 10C:
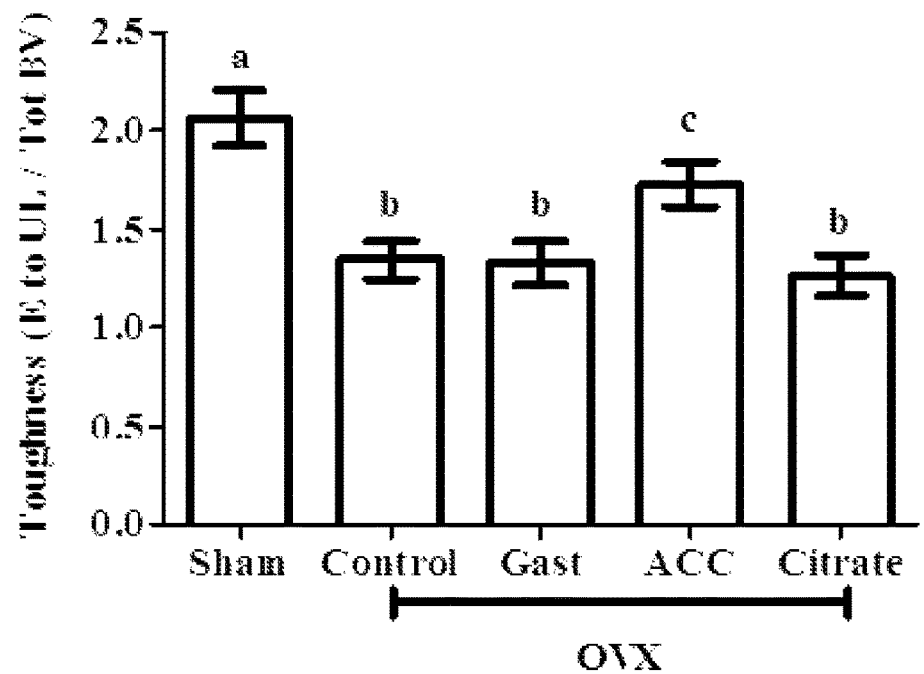
Figure 10D:
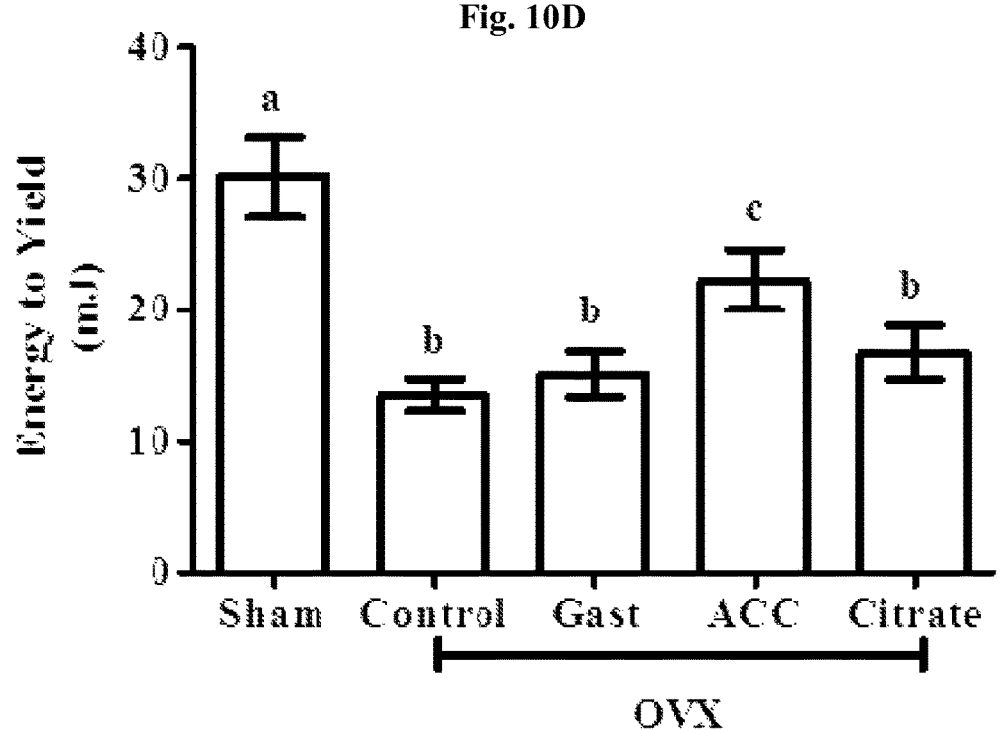
Figure 10E:
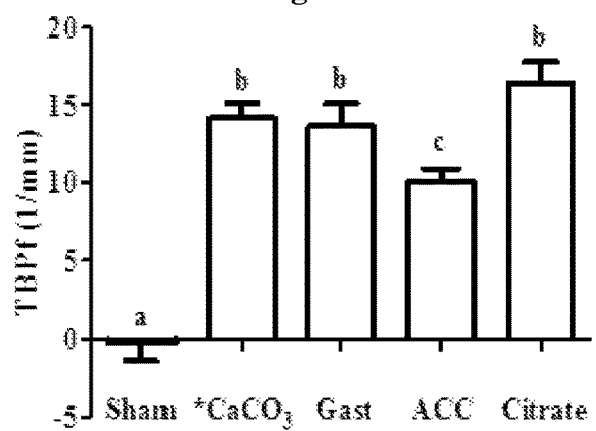
Figure 10F:
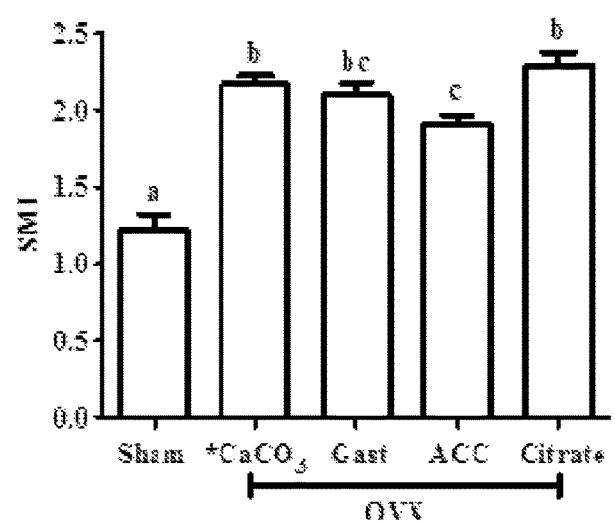
Figure 10G:
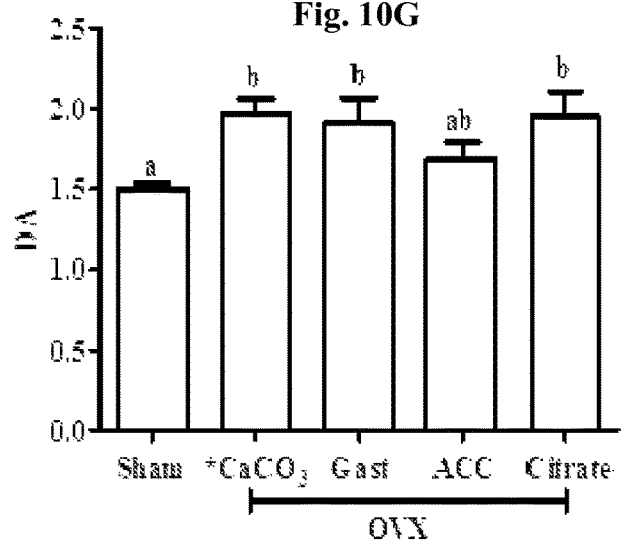

Ultimate Force (FIG. 10A); Energy to ultimate force (UF) (FIG. 10B); Toughness (FIG. 10C); Energy to yield (FIG. 10D); Trabecular bone pattern factor (TBPf) (FIG. 10E); Structure model index (SMI) (FIG. 10F); Degree of anisotropy (DA) (FIG. 10G).

One-way ANOVA: $p<0.01$. Letters represent Fishers LSD post-hoc comparison. Bars represent SEM.

DETAILED DESCRIPTION OF THE INVENTION

The present invention discloses a previously unknown use of compositions comprising stable amorphous calcium carbonate (ACC). The amorphous calcium carbonate based compositions according to the present invention were found to be superior calcium sources over commonly marketed calcium supplements. It has now been found that a composition comprising ACC has a surprisingly high calcium bioavailability, comprising higher absorbability in the gastrointestinal tract and in the bones. Thus the use of ACC is beneficial in calcium malabsorption associated disorders, diseases and conditions (both in fed and even greater advantage in fasting state) and in bone loss related disorders and conditions.

The term "treatment" as employed herein refers to the administration of ACC and enhancement of calcium absorption in gastrointestinal tract and in bones.

The terms "delaying the onset" or "prophylaxis" as employed herein refer to the postponement of development of the bone diseases, postponement of development of symptoms and/or a reduction in the severity of such symptoms that will or are expected to develop.

The term "stable ACC" is used herein to indicate that the calcium carbonate is maintained in the amorphous state for long periods of time, e.g., from several weeks to several years, with no more than 5% conversion into the crystalline form over the said period of time. The crystallization of the ACC is inhibited according to the invention by the addition of one or more stabilizer, selected from organic or inorganic ingredients such as phosphorylated amino acids, other organic acids, peptides, salts, saccharides, or lipids. Said salts may comprise, for example, cations selected from magnesium, potassium, strontium, and sodium, and anions selected from carbonate, phosphate, sulfate, chloride, bromide, fluoride, citrate, fumarate, malate or other organic anions; the terms anion and cation are used to simply describe the salt composition, without implying anything about the solubility or pH of the said molecules.

The terms "stabilizer" or "stabilizing agent" as used herein are used interchangeably and refer to any substance that preserves calcium carbonate in the amorphous state.

The term "calcium malabsorption" as used herein refers to abnormality in absorption of dietary calcium across the gastrointestinal tract. The term "bone loss" as used herein refers to any decrease in bone cells or tissue, decrease in bone mass, decrease of bone minerals, or decrease of bone mineral density in a subject.

The term "effective amount" as used herein refers to a sufficient amount of the compositions of comprising stable ACC to treat calcium malabsorption, calcium malabsorption and mineral bone density associated diseases, disorders and conditions and to enhance mineral bone density at a reasonable benefit/risk ratio applicable to any medical or nutritional treatment.

In one embodiment, the present invention provides a synthetic (artificial) composition comprising stable ACC and an amount of a stabilizer sufficient to maintain the ACC in a non-crystalline state. The stabilizer is selected from, but not limited to, organic acids, phosphoric or sulfuric esters of hydroxylcarboxylic acids and hydroxyl bearing organic compounds. According to some embodiments, said stabilizer comprises at least one component selected from phosphoric or sulfuric esters of hydroxylcarboxylic acids, such as phosphoenolpyruvate, phosphoserine, phosphothreonine, sulfoserine or sulfothreonine and hydroxyl bearing organic compounds, selected from mono-, di-, tri-, oligo- and polysaccharides, for example, sucrose, mannose, glucose. The stabilizer comprising hydroxyl bearing compound may further comprise at least one alkali hydroxide, such as sodium hydroxide, potassium hydroxide and the like. In some embodiments of the invention, said stabilizer is selected from phosphorylated amino acids and polyols. The phosphorylated acids may be present in oligopeptides and polypeptides. In other embodiments of the invention, the stabilizer is an organic acid, preferably a carboxylic acid. The carboxylic acid is preferably selected from citric acid, tartaric acid or malic acid.

In one embodiment of the invention, the ACC is stabilized by phosphoserine (P-Ser) or phosphothreonine (P-Thr). In another embodiment, the stable ACC comprises a combination of sucrose and sodium hydroxide. In still another embodiment of the invention, the ACC is stabilized by citric acid. In yet another embodiment of the invention, the ACC is stabilized by a combination of phosphoserine and citric acid. In a preferred embodiment of the invention, an artificial composition comprising stable ACC comprising traces of one or more stabilizers is administered to a person in need of increased or improved calcium absorption.

In another embodiment, the present invention provides a natural composition, comprising stable ACC present in isolated crayfish gastrolith. The ground gastrolith comprises ACC, organic matter consisting mainly of chitin and polypeptides, and salts. The components present in the organic matter stabilize the ACC and prevent its crystallization.

In one aspect, the high calcium bioavailability presented in the inventions is not related to the stabilizing molecule. In another aspect, the present invention claims that the high calcium bioavailability is only related to the amorphous state of the calcium carbonate.

In another aspect, the present invention provides a composition comprising stable ACC, comprising at least one stabilizer for use in treatment of calcium malabsorption in patients suffering from calcium malabsorption and calcium malabsorption associated disorders, diseases and conditions. In another aspect, there is provided a method for the enhancement of calcium gastrointestinal absorption in a subject suffering from calcium malabsorption, comprising administering to said subject an effective amount of a composition comprising stable amorphous calcium carbonate, comprising at least one stabilizer.

According to some embodiments conditions related to calcium deficiency include patients after bariatric or gastric surgery, patients suffering from hypoparathyroidism, vitamin D deficiency, renal tubular diseases, renal failure, pancreatitis, hypoproteinemia, and hyperphosphatemia. According to alternative embodiments diseases involving calcium malabsorption include Crohn's disease, cystic fibrosis, inflammatory bowel disease, celiac disease, and atopic gastritis. According to further embodiments calcium malabsorption may encompass subjects with enhanced bone formation and individuals consuming corticosteroids, proton pump inhibitors, anticonvulsants, rifampin and similar antibiotics, chelating agents, and antisecretory drugs.

Reduced calcium gastrointestinal absorption may further lead to bone mineral density loss.

In another aspect, the present invention provides compositions comprising stable ACC, comprising at least one stabilizer for use in increasing mineral bone density in patients suffering from calcium malabsorption associated disorders, diseases and conditions. The present invention further provides a composition comprising stable ACC comprising at least one stabilizer for treatment of bone density loss in a subject suffering from calcium malabsorption. Enhanced calcium gastrointestinal absorption of stable ACC compared to other calcium supplements may delay or minimize conditions and disorders resulting from calcium deficiency in populations including postmenopausal women, and perimenopausal women, elderly men, children, adolescents, pregnant women, and breastfeeding women.

In yet another aspect, the present invention provides a composition comprising stable ACC comprising at least one stabilizer for use in enhancement of bone mineral density in bone metabolism associated disorders, diseases or conditions. According to one embodiment of the invention, the bone metabolism associated disorders, diseases and conditions are selected from oseomalacia, Paget's disease of bone, osteopenia, osteitis fibrosa cystica, Rickets, osteoporosis and acute alcohol consumption. According to some embodiments, said composition may be administered in combination with other medications for prevention and treatment of bone loss. The medications for prevention and treatment of bone loss are selected from bone resorption inhibitors, comprising bisphosphonates (salts of bisphosphonic acid), estrogen receptor modulators, androgen receptor modulators, calcitonin formulations, alpha-calcitonin gene-related peptide formulations, ipriflavone formulations, anabolic steroid formulations, anti-RANKL (receptor activator of NF-kappa B ligand) antibody and the like. One non-limiting example of a bisphosphonate used for prevention or treatment of bone mineral density loss is the bisphosphonate Alendronate. The use of a composition comprising ACC in combination with bone resorption inhibitors provides an additive effect on increasing bone mineral density. Without wishing to be bound by any specific theory, the additive effect provided by ACC may be attributed to the high bioavailability and bone-formation inducing effect thereof. Administration of ACC in combination with bone resorption inhibitor allows the reduction of therapeutic doses of bone resorptive inhibitor due to the observed additive effect, as compared to administration of ALN in combination with crystalline calcium carbonate. In some embodiments, the invention provides a method for enhancing bone mineral density in bone metabolism associated disorders, comprising administering a composition comprising stable ACC comprising at least one stabilizer in combination with bisphosphonates. In the context of the present invention the term combination therapy encompasses administration of two or more active ingredients in a single dosage form or in separate dosage forms. Separate dosage forms may be administered simultaneously or sequentially or on entirely independent separate regimens. For example, the ACC may be administered daily and the bisphosphonate may be administered less frequently.

In some embodiments, said composition is administered in combination with lower therapeutical doses of bisphosphonate, compared to the dose required without calcium supplements or with calcium supplements other than stable ACC supplements e. In some embodiments, the bisphosphonate is Alendronate. In some embodiments, said composition is administered in combination with lower therapeutical doses of Alendronate, compared to the dose required without calcium supplements or with calcium supplements other than stable ACC supplements. In some embodiments, said composition in combination with ALN is used for enhancing bone mineral density in osteoporosis.

In yet another aspect, the present invention provides a composition comprising stable ACC, comprising at least one stabilizer for treatment of bone mineral density loss-associated disorders. According to one embodiment of the invention, the bone mineral density loss-associated disorders, diseases and conditions are selected from osteomalacia, osteopenia, osteitis fibrosa cystica, Rickets, osteoporosis and acute alcohol consumption.

In still another aspect, the present invention provides a composition comprising stable ACC, comprising at least one stabilizer for delaying the onset or prophylaxis of bone mineral density loss-associated disorders. According to one embodiment of the invention, the bone mineral density loss-associated disorders, diseases and conditions are selected from osteomalacia, osteopenia, osteitis fibrosa cystica, Rickets, osteoporosis and acute alcohol consumption.

According to the method of the present invention, the composition comprising stable ACC is particularly advantageous for use in subjects susceptible to decrease in bone mineral density or to the development of a bone metabolism associated disorder, such as postmenopausal women and elderly men. In another aspect, the compositions of the invention are administered to subjects required to consume high levels of calcium such as children, adolescents and women during pregnancy and breastfeeding. In yet another aspect, the compositions of the invention are administered to subjects suffering from calcium malabsorption.

In one aspect, the present invention relates to the use of compositions comprising stable ACC comprising at least one stabilizer in the preparation of medicaments for treatment of calcium malabsorption in patients suffering from calcium malabsorption associated disorders, diseases and conditions.

In a still further aspect, the present invention relates to the use of a composition comprising stable ACC comprising at least one stabilizer in the preparation of medicaments for enhancement of bone mineral density in a bone metabolism associated disorder, disease or condition. In some embodiments said medicaments are used in combination with bone resorption inhibitors. In a yet further aspect, said compositions are used in the preparation of medicine for treatment of bone mineral density loss associated diseases, disorders and conditions. In a still further aspect, the present invention relates to the use of a composition comprising ACC in the preparation of medicaments for prophylaxis of bone mineral density loss associated diseases, disorders and conditions and calcium malabsorption related conditions. In a still further aspect, the compositions of the present invention are used for increasing calcium absorption in populations susceptible to the development of metabolic bone disorders, diseases and conditions. In one embodiment, the present invention relates to the oral administration of a composition comprising stable ACC having a superior gastrointestinal bioavailability when administered in a fed state. In another embodiment, the present invention relates to the oral administration of a composition comprising stable ACC in a fasting state to reach a greater efficient gastrointestinal bioavailability.

Evidence has been provided, supporting the notion that it is the amorphous calcium carbonate alone, regardless of the stabilizing molecule or mechanism, that promotes the higher bioavailability of calcium when administered as ACC. In an important embodiment of the invention, synthetic ACC has a superior gastrointestinal bioavailability when administered in a fed state. In another important embodiment of the invention, synthetic ACC has a superior gastric bioavailability when administered in a fasting state. In a still other important embodiment of the invention, ACC from natural sources has a superior gastric bioavailability when administered in a fed state. In a further important embodiment of present invention, ACC from natural sources has a superior gastric bioavailability when administered in a fasting state. According to some embodiments, the administration of stable ACC comprising at least one stabilizer to a subject in need of such treatment is performed regardless of whether the subject is in a fasting state or in a fed state.

The compositions of the invention may be preferably administered orally in various oral forms including, but not limited to, tablets, capsules, pills, powders, granules, elixirs, tinctures, suspensions, syrups, emulsions and as gel form.

In instances in which oral administration is in the form of a tablet or capsule, the composition components can be combined with a non-toxic pharmaceutically acceptable inert carrier or excipients such as lactose, starch, sucrose, glucose, modified sugars, modified starches, methylcellulose and its derivatives, mannitol, sorbitol, and other reducing and non-reducing sugars, magnesium stearate, stearic acid, sodium stearyl fumarate, glyceryl behenate, amorphous silica gel or other desiccant material and the like.

The compositions of the invention may be administered in daily doses of from 0.5 to about 5 g. According to alternative embodiments, the compositions of the invention may be administered in daily doses of from 1.5 to about 20 g. The compositions of the invention may be administered in daily doses comprising elemental calcium in a range of from 0.15 to about 1.5 g. According to alternative embodiments, the compositions of the invention may typically be administered in daily doses comprising elemental calcium in a range of from 0.5 to about 6 g.

For oral administration in liquid form, the composition components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture.

A particular advantage of the compositions according to the invention is their confirmed low toxicity and high safety for oral administration. Accordingly, the compositions of the invention are, in other aspect of the invention, advantageously used as medical foods.

The inventors have conducted experiments aiming to evaluate the bioavailability of calcium source comprising stable ACC. The bioavailability of calcium from ACC was evaluated both in terms of calcium gastrointestinal absorption and of calcium availability to bone mineralization process (bone absorbability). The gastrointestinal absorption of calcium in generally healthy population and in population suffering or susceptible to suffering from calcium malabsorption was assessed. Reduced calcium gastrointestinal absorption is one of the causes of bone density loss. Therefore, calcium bone absorbability in populations suffering from calcium malabsorption was also assessed. The use of stable ACC may be beneficial for enhancing calcium gastrointestinal absorption and for increasing bone mineral density in subjects suffering or susceptible to suffering from calcium malabsorption. Calcium gastrointestinal absorption was further evaluated in populations susceptible to the bone loss-related disorders and conditions, e.g. postmenopausal women.

The enhanced calcium availability to bone mineralization process was found to increase bone mineral density and to positively affect other bone parameters. As exemplified hereinbelow, the effect of stable ACC comprising different stabilizers on various bone parameters was evaluated. The effect of ACC on bone mineral density and other bone parameters in the osteoporotic rat model was also evaluated. Amorphous calcium carbonate based compositions were also combined with bone anti-resorptive medications, such as Alendronate bisphosphonate and their mutual effect on bone fraction parameters was evaluated.

The bioavailability measurements comprised the evaluation of calcium absorption from stable ACC source in the gastrointestinal tract by means of serum and urine sampling, based on widely reported bioavailability models used for the assessment of various drugs and supplements, and the evaluation of the effect of calcium from stable ACC source on bone mineral density and other bone parameters, based on the widely reported osteoporosis prevention and treatment models, used for the assessment of various drugs and supplements. The bioavailability of stable ACC was evaluated in patients suffering from malabsorption, e.g. patients suffering from hypoparathyroidism and individuals consuming corticosteroids and in populations suffering from bone mineral density associated disorders. The enhanced bioavailability of calcium from the ACC source allows use of ACC for treatment and prophylaxis of various calcium malabsorption and metabolic bone associated diseases, disorders and conditions alone or in combination with standard medications for treatment of bone loss. Having now generally described the invention, the same will be more readily understood through reference to the following examples, which are provided by way of illustration and are not intended to be limiting of the present invention.

EXAMPLES

Trial 1: Gastrointestinal Absorption of Calcium from ACC Source.

The objective of the present experiment was to evaluate gastrointestinal absorption of the calcium source comprising stable Amorphous Calcium Carbonate (ACC) in the rat radioisotope labeling model.

Twenty-six 2 month-old male Wistar rats, weighing 240±15 g, were orally administered with a single gelatin capsule containing either ACC (amorphous calcium carbonate) or CCC (crystalline calcium carbonate) intrinsically labeled with $^{45}Ca$, followed by measurements of calcium fractional absorption in serum and calcium excretion.

Figure 1:
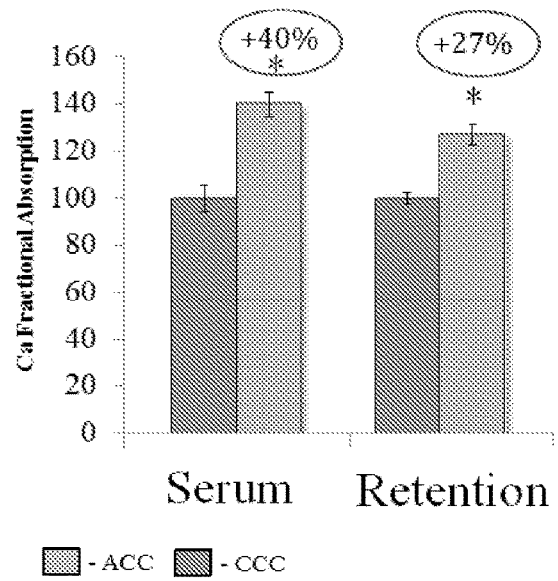
FIG. 1: Calcium levels are elevated following amorphous calcium carbonate (ACC) vs. crystalline calcium carbonate administration to rats Results are means±SEM Student's t-test: *$p<0.05$

FIG. 1 presents the changes in serum calcium concentration, as calculated by the radioactive readings normalized to the administered dose. The C. values in rats that received ACC were significantly higher (up to 40%) than those in the CCC group (FIG. 1 and Table 1).

TABLE 1

Pharmacokinetic parameters of calcium in the serum following oral administration of radioactive calcium carbonate preparations

| Compound | $C_{max}$ (μg/mL) | $T_{max}$ (h) | $AUC_∞$ (μg × h/mL) |
|---|---|---|---|
| CCC | 5.8 ± 0.07 [a] | 3.0 ± 0.3 [a] | 109.7 ± 6.4 [a] |
| ACC | 8.1 ± 0.8 [b] | 2.8 ± 0.2 [a] | 134.5 ± 7.0 [b] |

Different superscript letters represent statistical significance (p < 0.05), as determined by ANOVA Pharmacokinetic analysis indicates that the gastrointestinal absorption of the ACC is significantly higher than that of CCC (area under curve, AUC, values are higher by 22.5% and 20%, respectively, p<0.05), while the time required to reach the maximal concentration ($T_{max}$) did not differ between groups (Table 1).

The retention values presented in FIG. 1 suggest that rats that received CCC-containing capsules retained 48.5±1.3% of the received dose. On the other hand, rats that received ACC capsules retained 61.4±2.0% and 60.6±2.1% of the received dose, respectively. This corresponds to a significant increase in retention of 26.6%, as compared to the retention by the CCC-treated group (p<0.05).

Experimental Details

Animals

All animals were treated according to the Israel Animal Welfare Act under the supervision of the Ben-Gurion University Animal Care and Use program. Fifty-one two month-old male Wistar rats (Harlan-Teklad, Jerusalem, Israel), weighing 240±15 g, were randomly housed in 12 stainless steel cages in an environmentally-controlled room (23° C. temperature, 12:12 h light:dark cycle). The rats were fed laboratory rat chow pellets adequate in nutrients ad libitum (Koffolk, Petah-Tikva, Israel) and had free access to water for 48 h. Four days before the beginning of the experiment, the regular diet was replaced with a low calcium diet containing 0.24±0.05% calcium (0.675±0.05% phosphate), specially prepared by mixing two food types containing, respectively, 0.01% calcium (0.3% phosphate; Harlan-Teklad) and 1% calcium (0.8% phosphate; Koffolk). The two food types were separately ground in a mill to yield two powders which were dry mixed in a ratio of 4:1, respectively, until fine homogenization. The homogenized powder was extruded to form new food pellets.

Seventeen hours prior to capsule administration, the rats were weighed and blood samples were taken (baseline). The rats were then placed into individual metabolic cages and deprived of food and water until 3 h post-capsule administration. Three and 24 h post-dosing, ~10 g of low calcium food pellets (0.01% calcium; Harlan-Teklad) were given to each rat. Distilled water was allowed ad libitum starting three h post-capsule administration.

Gelatin Capsule Administration to Animals

Each rat was lightly sedated for 30 seconds with isoflurane (Minrad) diluted 1:4 (v:v) with propylene glycol (Bio-Lab). A single capsule containing a specific calcium carbonate preparation (i.e. CCC, ACC, or ACC-C; n=17 for each group) was administered intragastrically to each of the experimental rats using a stainless steel rat administration syringe (Harvard Apparatus).

Animals Blood Sampling and Chemical Analysis

Blood samples of 120-150 μA were taken from each rat's tail vein 17 h prior to capsule administration (time 0) and 2, 3, 6, 10, 24 and 34 h post-administration. The blood samples were immediately centrifuged for 10 minutes at 3000 g using a tabletop centrifuge (Hettich Zentrifugen, Bach, Switzerland). Duplicate samples (30 μl) of the supernatant serum were transferred into plastic vials containing scintillation liquid (Zinsser Analytic, Berkshire, UK) and radioactivity was measured using a liquid scintillation counter (Tri-Carb 2100TR, PerkinElmer, Boston, Mass.). Plasma radioactivity from the given dose were normalized according to the measured radioactivity and specific radioactive dose that each rat received [(serum cpm×100)/(total cpm× sample volume)].

Animal Feces and Urine Sampling and Analysis)

Feces and urine were collected during the 17 h starvation phase during the acclimation period (baseline) and during the entire 34 h of the experiment to evaluate calcium. Samples of urine (500 μL) were transferred into plastic vials filled with scintillation liquid. Feces were dried overnight at 70° C. in an oven. The samples were ground in a mortar until fine homogenization. Feces samples (200 mg) were placed into 5 ml of 1 N NaOH solution (Gadot, Netanya, Israel), incubated for 3 hours at 80° C. and centrifuged for 10 minutes at 3,600 g. Duplicate samples of the supernatant (30 μL) were transferred into plastic vials containing scintillation liquid. Radioactivity of the urine and feces samples was measured using a liquid scintillation counter. Retention values were calculated by subtracting the radioactivity measured in the feces and urine from the given dose [(intake− feces and urine excretion)/(intake×100%)].

Pharmacokinetic Calculations of Animal Samples

Non-compartmental analysis of an individual rat's calcium concentration versus time data was performed using WinNonLin 5.2 software (Pharsight, Mountain View, Calif.).

Statistical Analysis

One-way analysis of variance (ANOVA) was performed on retention values, pharmacokinetic results and solubility results using the Statistica 6.1 software (StaSoft, Tulsa, Okla.).

Paired t-test and student's t-test were performed using Prism 5 software.

A p value <0.05 was deemed significant.

The results of the above trial confirmed that stable ACC has higher gastrointestinal absorption than CCC in an animal model.

Trial 2: Calcium Gastrointestinal Absorption in Hypoparathyroidism

The experiment aiming to evaluate gastrointestinal bioavailability of the calcium source comprising stable Amorphous Calcium Carbonate (ACC) in the treatment of calcium malabsorption is conducted. A randomized, two phase, adaptive then crossover open-label, study is performed, comparing amorphous calcium carbonate (ACC) supplement to commercially available crystalline calcium supplements (CCS) in the management of primary hypoparathyroidism.

The primary objective of the first phase of the trial is a proof of concept that treatment with smaller doses of elemental calcium from ACC compared to crystalline calcium supplement (CCS) can maintain target serum calcium (corrected for albumin) values (7.0-10.0 mg/dL). The secondary objective of the first stage is to evaluate the sufficient ACC dose. The further secondary objective is to determine the effect of food on ACC absorption.

The primary objective of the second phase of the trial is testing the hypothesis that treatment with smaller doses of elemental calcium from ACC compared to CCS can maintain target serum calcium (corrected for albumin) values (7.0-10.0 mg/dL). The secondary objective of the first stage is testing the hypothesis that treatment with smaller doses of elemental calcium from ACC compared to CCS does not cause an increase in hypercalciuria in subjects with hypoparathyroidism. The further secondary objective is testing the hypothesis that treatment with smaller doses of elemental calcium from ACC compared to CCS reduces the side effects related with high calcium consumption.

Selection of Study Population

The study population includes twenty (20) subjects with primary hypoparathyroidism, 10 subjects for each phase.

Investigational Product

The stable amorphous calcium carbonate used in the study is a synthetic ACC stabilized by low concentrations of phosphoserine and citrate (less than 0.5% in the final product), provided by Amorphical Ltd. Phosphorylated serine and the organic citric acid are non-toxic, naturally abundant and even consumed as a standalone dietary supplements with no reported adverse effects when taken orally.

Table 2 summarizes the ACC chemical analysis, assessed according to the U.S. Pharmacopeia parameters of calcium carbonate, using Inductively Coupled Plasma Atomic Emission (ICP-AE), Ultraviolet (UV) Spectroscopy, Loss on Ignition (LOI) and flame photometer. Unless otherwise specified, the accuracy of the measured values is ±10%.

TABLE 2

Chemical analysis of Amorphical ACC.

| Analysis | USP requirements | ACC analysis result |
| --- | --- | --- |
| Loss On Ignition (LOI) | N/A | 14.8% |
| Ethanol residues | N/A | 0.034% |
| Acid Insoluble | Less than 0.2% | Less than 0.0002% |
| Calcium | N/A | 32.5% |
| Chlorides | N/A | 1.36% |
| Sodium | N/A | 1.85% |
| Phosphorus | N/A | 0.143% |
| Sulfur | N/A | <0.1% |
| Iron | Less than 1,000 ppm | 9.5 ppm |
| Alkali metals* | Less than 10,000 ppm | 475 ppm |
| Barium** | Pass flame test | 20 ppm |
| Mercury | Less than 0.5 ppm | Less than 1 ppm*** |
| Fluorides | Less than 0.005% | 0.001% |
| Lead | Less than 3 ppm | Less than 5 ppm*** |
| Heavy metals | Less than 0.002% | Trace (Less than 0.002%) |
| Arsenic (total) | Less than 3 ppm | Less than 3 ppm |
| Crystalline Calcium Carbonate | Less than 5% | Less than 1% |

*Not including sodium.
**Cannot be performed according to the USP (was performed in Inductive Coupled Plasma (ICP)).
***Interferences in the ICP measurements prevented lower concentration analyses.

Control Product—Standard of Care

Treatment of patients with hypoparathyroidism involves correcting the hypocalcemia by administering calcium and vitamin D (Cusano et al, 2012; Fong & Kahn, 2012). Oral supplementation is started with elemental calcium (1-2 g 3 times daily) and calcitriol (0.25-1 μg 2 or 3 times daily) for immediate management of postsurgical hypoparathyroidism. In patients at risk of severe and/or prolonged hypocalcemia, elemental calcium is started at a dosage of 2 g 3 times daily and calcitriol at a dosage of 0.5 μg 3 times daily. There are several types of calcium supplementation. It is available with or without a prescription. All of them moderates nerve and muscle performance and facilitates normal cardiac function (Straub, 2007):

Calcium Carbonate (Tums extra strength, Cal-plus, Caltrate, Os-Cal 500)—Amongst all available calcium supplements' formulations, calcium carbonate is one of the most concentrated calcium supplements with 40% elemental calcium. Many commercially available preparations exist. Total daily dose of elemental calcium needs to be titrated to minimize the daily dose of vitamin D and to keep patients asymptomatic. Ionized calcium is absorbed best in an acidic environment; 400 mg elemental calcium equals 1 g calcium carbonate.

Calcium Citrate (Citracal, Cal-Cytrate 250)—210 mg of elemental calcium equals 1 g calcium citrate.

Calcium Gluconate (Kalcinate)—Available for IV use. Infuse slowly over 5-10 min; 10 mL calcium gluconate contains approximately 90 mg elemental calcium; 1000 mg of calcium gluconate equals 90 mg elemental calcium.

In the present study, patients in the control group continue to consume their regular calcium supplements and thus are treated with standard-of-care.

Dosage and Administration

Phase 1

Eligible subjects receive ACC tablets. Each dose of the study investigational product consists of 50 or 200 mg of elemental calcium from ACC in each tablet.

Phase II

Eligible subjects receive ACC tablets in a crossover study design. The control arm is treated with a standard of care (by taking their regular calcium supplementation). Each dose of the study investigational product consists of 50 or 200 mg of elemental calcium from ACC in each tablet.

TABLE 3

Dose of Study Treatment

| Group | Treatment |
| --- | --- |
| INVESTIGATIONAL PRODUCT | Tablets, each containing 50 or 200 mg of elemental calcium from ACC, for oral use. |
| CONTROL PRODUCT | Standard of care. |

The mechanism of action and the effect of ACC are yet to be revealed. Therefore, selection of the dosage and the favorable absorption conditions (fed/fasted) is based on the results of phase I of the study. While the final dosage has to be determined specifically for every patient, it is expected that it will be possible to determine a conversion factor between ACC and CCS that will allow easy conversion between both formulas.

The calcium dosage in the control arm is determined according to the known medical history and medication routine of each and every patient.

The tablets administration is performed 3 times a day throughout the treatment period by the subject. IPs administration is documented in the Case Report Forms (CRF) in each visit to the Clinical Research Center (CRC) IP Administration Records. Packs with unused tablets are returned to the CRC unit in visits days, counted and documented in the CRFs.

Allocation of Subjects to Treatment

Subjects are assigned to one of the treatment groups randomly according to a randomization list. Randomization is performed using block randomization.

Blinding

This is an open-label study. The subjects, the investigators and any personnel involved in subjects' assessment, monitoring, analysis and data management are not blinded to the subject formulation assignment. The Sponsor is responsible for preparing, dispensing and labeling the investigational product IP.

Study Design

The Study Consists of Two Phases:

Phase I

Ten (10) subjects previously diagnosed and chronically treated for primary hypoparathyroidism are enrolled. The daily CCS intake is gradually replaced by reduced amount of elemental calcium from ACC. Five (5) subjects consume the ACC before having a meal and the other five (5) subjects consume the ACC after having a meal. The safety and the efficacy of the treatment are closely monitored throughout this phase.

The absorption of ACC is evaluated using weekly serum calcium corrected for albumin (CA) value tests. Excretion of calcium in urine is tested at screening and at the end of phase I.

Phase II

Ten (10) new subjects previously diagnosed and chronically treated for primary hypoparathyroidism are enrolled.

The subjects are randomly assigned to one of the following treatments for 6 weeks:
1. Standard of care—The same elemental calcium formulation and dosage that was used routinely prior to the study.
2. ACC—The established dosage of elemental calcium from ACC (based on the conversion factor and the fed/fasted conditions found in phase I of the study).

The two formulations are administered with the regular daily dosage of vitamin D (1-alfa D3).

At the end of the treatment, each group receives the alternative formulation for another 6 weeks.

The superior absorption of ACC is evaluated using weekly blood tests to calculate serum CA values. Excretion of calcium in urine is tested at screening and in the end of each treatment.

The following is a detailed description of the study procedures:

Eligible subjects are treated as follows:

Phase I

I-Day −21 (+/−17) Screening: Subjects with a diagnosed primary hypoparathyroidism (see section 4.1 for definitions), and who are treated with calcium and vitamin D supplementation at least 1 year prior to the beginning of the study and are without major renal or hepatic disease, are invited to the CRC. At the clinic, subjects are interviewed, their medical history and their current medication are documented and they sign an informed consent form (ICF). Subjects are referred to perform blood tests for serum calcium, P, creatinine and albumin levels. Calculation of albumin corrected calcium (CA) is performed. Subjects are instructed to perform 24 hour urine collection for Ca, P and creatinine. Subjects are asked to fill out a food and medication diary for 3 consecutive days to evaluate their daily dietary calcium intake. Women of childbearing age undergo a urine pregnancy test. Eligible subjects, complying with all inclusion criteria and having none of the exclusion criteria are enrolled to the study.

Subjects are informed by phone or on site whether they are eligible to enter the study.

I-Day 0: Eligible subjects arrive at the CRC where they are asked about any changes in their medical condition since their last visit. Blood tests are performed to define serum calcium, P and albumin baseline values. Calculation CA at baseline is performed.

Subjects receive a pack of ACC tablets, each tablet containing 50 or 200 mg elemental calcium (according to the daily total amount of calcium supplementation, 14 day supply+5 spare tablets). The replacement of CCS with ACC is calculated according to the following formula:

$$NTDC=ITDC-[0.1 \times ITDC(mg\ CCS)]+[0.05 \times ITDC(mg\ ACC)]$$

*ITDC—Initial total daily calcium intake (mg)
**NTDC—New total daily calcium intake (mg)

10% (in mg) out of the initial total daily intake of elemental calcium is replaced by 5% of elemental calcium from ACC (in mg, calculated out of the initial total daily intake). The daily intake of vitamin D remains the same.

The calculation for the number of tablets per day is performed specifically for each subject (according to the daily dosage of calcium supplementation) by the doctor.

Subjects are instructed to take the amount of ACC tablets a day, in accordance with their individual calculated NTDC:
1. Five subjects are instructed to take tablets in the morning after a meal, in midday after a meal and in the evening after a meal.
2. Five subjects are instructed to take tablets in the morning before having a meal, in midday before having a meal and in the evening before having a meal.

Subjects are instructed to continue their routine medications consumption during the trial.

I-Day 3 (±1): Subjects arrive at the CRC and their serum calcium, P and albumin levels are tested. Calculation of CA is performed to exclude hypocalcemia (Ca<7.0 mg/dL). If CA values are within the desired target range (7.0-10.0 mg/dl), subjects continue to take the calcium doses that were instructed on I-day 0. If CA values are below 7.0 mg/dl or above 10.0 mg/dl, changes to the calcium intake are made, according to the doctor's decision.

I-Day 7 (±1): Subjects arrive at the CRC and their serum calcium, P and albumin levels are tested. Calculation of CA is performed:

a. Conversion factor 0.5:

If CA=baseline, then 20% (in mg, calculated out of the initial total daily intake) of elemental calcium is replaced by 10% of elemental calcium from ACC (in mg, calculated out of the initial total daily intake).

$$NTDC=ITDC-[0.2 \times ITDC(mg\ CCS)]+[0.1 \times ITDC(mg\ ACC)]$$

b. Conversion factor 0.75:

If CA<baseline, then 10% (in mg, calculated out of the initial total daily intake) of elemental calcium is replaced by 7.5% of elemental calcium from ACC (in mg, calculated out of the initial total daily intake).

$$NTDC=ITDC-[0.1 \times ITDC(mg\ CCS)]+[0.075 \times ITDC(mg\ ACC)]$$

CA<7.00 mg/dl enforces end of treatment.

c. Conversion factor 0.25:

If CA>baseline, then 10% (in mg, calculated out of the initial total daily intake) of elemental calcium is replaced by 2.5% of elemental calcium from ACC (in mg, calculated out of the initial total daily intake).

$$NTDC=ITDC-[0.1\times ITDC(mg\ CCS)]+[0.025\times ITDC(mg\ ACC)]$$

Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression). Subjects receive instructions regarding the new doses of ACC and are reminded to take the amount of tablets a day in accordance with their individual calculated NTDC), in the morning, in midday and in the evening, before or after a meal (based on their initial assignment). Subjects are reminded to continue their routine medications consumption during the trial.

I-Day 10 (±1): Subjects arrive at the CRC and their serum calcium, P and albumin levels are tested. Calculation of CA is performed to exclude hypocalcemia (Ca<7.0 mg/dL). If CA levels are within the desired target range (7.0-10.0 mg/dl), subjects continue to take the calcium doses that were instructed on I-day 7. If CA levels are below 7.0 mg/dl or above 10.0 mg/dl, changes to the calcium intake are be made, according to the doctor's decision.

I-Day 14 (±1): Subjects arrive at the CRC and their serum calcium, P and albumin levels are tested. Calculation of CA is performed to exclude hypocalcemia (Ca<7.0 mg/dL). If none of the conversion formulas (a-c, I-Day 7) resulted in serum calcium values within the desired target range (7.0-10.0 mg/dL), the study is terminated.

Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression).

50% of the initial daily supplementation of CCS is replaced by ACC based on the conversion factor found in I-day 7 (formulas a-c):
 a. Conversion factor 0.5: 50% (in mg, calculated out of the initial total daily intake) of elemental calcium is replaced by 25% of elemental calcium from ACC (in mg, calculated out of the initial total daily intake).

$$NTDC=ITDC-[0.5\times ITDC(mg\ CCS)]+[0.25\times ITDC(mg\ ACC)]$$

b. Conversion factor 0.75: 50% (in mg, calculated out of the initial total daily intake) of elemental calcium is replaced by 37.5% of elemental calcium from ACC (in mg, calculated out of the initial total daily intake).

$$NTDC=ITDC-[0.5\times ITDC(mg\ CCS)]+[0.375\times ITDC(mg\ ACC)]$$

c. Conversion factor 0.25: 50% (in mg, calculated out of the initial total daily intake) of elemental calcium is replaced by 12.5% of elemental calcium from ACC (in mg, calculated out of the initial total daily intake).

$$NTDC=ITDC-[0.5\times ITDC(mg\ CCS)]+[0.125\times ITDC(mg\ ACC)]$$

Subjects receive a pack of ACC tablets, each tablet containing 50 or 200 mg elemental calcium (according to their individual calculated NTDC, 14 day supply+5 spare tablets). Subjects receive instructions regarding the new doses of ACC and are reminded to take the amount of tablets a day in accordance their individual calculated NTDC, in the morning, in the midday and in the evening, before or after a meal (based on their initial assignment). Subjects are reminded to continue their routine medications consumption during the trial.

I-Day 21 (±1): Subjects arrive at the CRC and their serum calcium, P and albumin levels are tested. Calculation of CA are performed to exclude hypocalcemia (Ca<7.0 mg/dL). Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression). If CA levels are below 7.0 mg/dl, or above 10.0 mg/dl, subject is excluded from the study (based on the doctor's decision). If CA levels are within the desired target range (7.0-10.0 mg/dL), a complete replacement of the daily supplementation of CCS with ACC is performed, based on the conversion factor found in I-day 7 (formulas a-c):
 a. Conversion factor 0.5: 100% (in mg) of the elemental calcium initial total daily intake is replaced by 50% of elemental calcium from ACC (in mg, calculated out of the initial total daily intake).

$$NTDC=ITDC-[ITDC(mg\ CCS)]+[0.5\times ITDC(mg\ ACC)]$$

b. Conversion factor 0.75: 100% (in mg) of the elemental calcium initial total daily intake is replaced by 75% of elemental calcium from ACC (in mg, calculated out of the initial total daily intake).

$$NTDC=ITDC-[ITDC(mg\ CCS)]+[0.75\times ITDC(mg\ ACC)]$$

c. Conversion factor 0.25: 100% (in mg) of the elemental calcium initial total daily intake is replaced by 25% of elemental calcium from ACC (in mg, calculated out of the initial total daily intake).

$$NTDC=ITDC-[ITDC(mg\ CCS)]+[0.25\times ITDC(mg\ ACC)]$$

Subjects receive instructions regarding the new doses of ACC and are reminded to take the amount of tablets a day in accordance their individual calculated NTDC, in the morning, in the midday and in the evening, before or after a meal (based on their initial assignment). Subjects are reminded to continue their routine medications consumption during the trial. Subjects receive a container to perform 24 hour urine collection prior to their next scheduled visit.

I-Day 27 (±1) by phone: Subjects are reminded to perform 24 hour urine collection.

I-Day 28 (±1)—Termination of phase I: Subjects arrive at the CRC and their serum calcium, P and albumin levels are tested. Calculation of CA is performed. Subjects provide the container of 24 hour urine collection for Ca, P and creatinine to test calciuria. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, and depression).

Phase I results are examined before deciding whether or not to embark on the crossover portion of the study planned for Phase II. Phase I data is summarized, showing for each subject, by arm and overall the relationship between CA levels by amount of ACC replacement of CCS received.

Phase II

Ten (10) new subjects previously diagnosed and chronically treated for primary hypoparathyroidism are enrolled.

The subjects are randomly assigned to one of the following treatments for 6 weeks:

1. Standard of care (CCS)— The same elemental calcium dosage that was used routinely prior to the study.
2. ACC—The established dosage of elemental calcium from ACC (based on the conversion factor and the fed/fasted conditions found in stage I of the study).

The two formulations are administered with the regular daily dosage of vitamin D (1-alfa D3).

At the end of the treatment, each group receives the alternative formulation for another 6 weeks.

The superior absorption of ACC is evaluated using weekly blood tests to calculate serum CA values. Excretion of calcium in urine is tested at screening and in the end of each treatment.

II-Day −21 (+/−17) Screening: Subjects with a diagnosed primary hypoparathyroidism, and who had been receiving calcium and vitamin D supplementation at least 1 year prior to the beginning of the study and are without major renal or hepatic disease, are invited to the CRC. At the clinic, subjects are interviewed, their medical history and their current medication are documented and they sign an informed consent form (ICF). Subjects are referred to perform blood tests for Calcium, P and albumin levels. Calculation of CA is performed. Subjects are instructed to perform 24 hour urine collection for Ca, P and creatinine levels. Subjects are asked to fill out a food and medication diary for 3 consecutive days to evaluate their daily dietary calcium intake. Women of childbearing age undergo a urine pregnancy test. Eligible subjects, complying with all inclusion criteria and having none of the exclusion criteria are enrolled to the study.

Subjects are informed by phone or on site whether they are eligible to enter the study.

II-Day 0: Eligible subjects arrive at the CRC where they are asked about any changes in their medical condition since their last visit. Blood tests are performed to define serum calcium, P and albumin baseline values. CA values are calculated at baseline.

Subjects are randomly assigned to one of the following treatments:
1. Standard-of-care (CCS)— The same elemental calcium dosage that was used routinely prior to the study.
2. ACC—The established dosage of elemental calcium from ACC (based on the conversion factor and the fed/fasted conditions found in stage I of the study).

Subjects that were assigned to the ACC treatment arm, receive a container with ACC tablets, each tablet containing 200 mg elemental calcium (35 day supply+5 spare tablet). Subjects assigned to the CCS treatment arm continue to take their routine calcium supplementation. The exact dosage of calcium supplementation is determined for each subject according the known medical history.

Subjects are instructed to continue their routine medications consumption during the trial.

II-Day 3 (±1): Subjects arrive at the CRC and their serum calcium, P and albumin levels are tested. Calculation of CA is performed to exclude hypocalcemia (Ca<7.0 mg/dL). If CA values are within the desired target range (7.0-10.0 mg/dl), subjects continue to take the calcium doses that were instructed on II-day 0. If CA levels are below 7.0 mg/dL or above 10.0 mg/dL, changes to calcium intake are made, according to the doctor's decision.

II-Day 7 (±1): Subjects arrive at the CRC and their serum calcium, P and albumin levels are tested. Calculation of CA is performed. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression). Adjustments of ACC or CCS intake are performed if necessary.

Subjects are reminded to take the calcium supplementation according to their assignment instructions.

Subjects are reminded to continue their routine medications consumption during the trial.

II-Day 10 (±1): Subjects arrive at the CRC and their serum calcium, P and albumin levels are tested. Calculation of CA is performed to exclude hypocalcemia (Ca<7.0 mg/dL). If CA levels are within the desired target range (7.0-10.0 mg/dl), subjects continue to take the calcium doses that were instructed on II-day 7. If CA levels are below 7.0 mg/dL, or above 10.0 mg/dL, changes to the calcium intake are made, according to the doctor's decision.

II-Day 14 (±1): Subjects arrive at the CRC and their serum calcium, P and albumin levels are tested. Calculation of CA is performed. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression).

Subjects are reminded to take the calcium supplementation according to their assignment instructions.

Subjects are reminded to continue their routine medications consumption during the trial.

II-Day 21 (±1): Subjects arrive at the CRC and their serum calcium, P and albumin are tested. Calculation of CA is performed. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression).

Subjects are reminded to take the calcium supplementation according to the instructions.

Subjects are reminded to continue their routine medications consumption during the trial.

Subjects receive a container to perform 24 hour urine collection prior to their next scheduled visit.

II-Day 34 (±1) by phone: Subjects are reminded to perform 24 hour urine collection.

II-Day 35 (±1): Subjects arrive to the CRC and their serum calcium, P and albumin levels are tested. Calculation of CA is performed. Subjects provide the container with 24 hour urine collection for Ca, P and creatinine to test calciuria. Subjects are asked about any side effects or AEs that may have occurred and changes in concomitant medications since their last visit.

Subjects are asked about symptoms and signs related with a change in serum calcium levels (tetany, facial grimacing, paresthesias, muscle aches, arrhythmia, depression).

Subjects previously assigned to the CCS treatment arm receive a pack of ACC tablets, each tablet containing 200 mg elemental calcium (35 day supply+5 spare tablets). Subjects previously assigned to the ACC treatment arm, are instructed to resume their regular CCS supplementation.

The exact dosage of calcium supplementation for each subject is determined by the known medical history.

Subjects are reminded to continue their routine medications consumption during the trial.

II-Day 38 (±1): Subjects arrive at the CRC and their serum calcium, P and albumin levels are tested. Calculation of CA is performed to exclude hypocalcemia (Ca<7.0 mg/dL). If CA levels are within the desired target range (7.0-10.0 mg/dl), subjects continue to take the calcium doses that were instructed on II-day 35. If CA levels are below 7.0 mg/dl or above 10.0 mg/dl, changes to the calcium intake are made, according to the doctor's decision.

II-Day 42 (±1): Subjects arrive at the CRC and their serum calcium, P and albumin levels are tested. Calculation of CA is performed. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression). Adjustments of ACC or CCS intake are performed if necessary.

Subjects are reminded to take the calcium supplementation according to their assignment instructions.

Subjects are reminded to continue their routine medications consumption during the trial.

II-Day 45 (±1): Subjects arrive at the CRC and their serum calcium, P and albumin levels are tested. Calculation of CA is performed to exclude hypocalcemia (Ca<7.0 mg/dL). If CA levels are within the desired target range (7.0-10.0 mg/dl), subjects continue to take the calcium doses that were instructed on II-day 42. If CA levels are below 7.0 mg/dl or above 10.0 mg/dl, changes to the calcium intake are made, according to the doctor's decision.

II-Day 49 (±1): Subjects arrive at the CRC and their serum calcium, P and albumin levels are tested. Calculation of CA is performed. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression).

Subjects are reminded to take the calcium supplementation according to their assignment instructions.

Subjects are reminded to continue their routine medications consumption during the trial.

II-Day 56 (±1): Subjects arrive at the CRC and their serum calcium, P and albumin levels are tested. Calculation of CA is performed. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression).

Subjects are reminded to take the calcium supplementation according to their assignment instructions.

Subjects are reminded to continue their routine medications consumption during the trial.

Subjects receive a container to perform 24 hour urine collection prior to their next scheduled visit.

II-Day 69 (±1) by phone: Subjects are reminded to perform 24 hour urine collection.

II-Day 70 (±1)—Termination of phase II: Subjects arrive at the CRC and their serum calcium, P and albumin levels are tested. Calculation of CA is performed. Subjects provide the container with 24 hour urine collection for Ca, P and creatinine to test calciuria. Subjects are asked about any side effects or AEs that may have occurred and changes in concomitant medications since their last visit. Subjects are asked about symptoms and signs related with a change in serum calcium levels (tetany, facial grimacing, paresthesias, muscle aches, arrhythmia, depression).

An unscheduled visit may be performed at any time during the study at the subject's request or as deemed necessary by the investigator. The date and reason for the unscheduled visit is recorded. All assessments are optional and to be conducted at the discretion of the investigator.

Early discontinuation visit occurs if a subject prematurely discontinued study participation (for the reasons specified in Section 7.4) and is similar to the Termination Visit (Day 28 in phase I, Day 70 in phase II).

The study procedures are summarized in tables 4 and 5.

Phase I

TABLE 4

Phase I procedure schedule.

| Assessment/Evaluation | Day | | | | | | | | | |
|---|---|---|---|---|---|---|---|---|---|---|
| | (−21) (±21) | *(−2) (±2) | 0 (±1) | 3 (±1) | 7 (±1) | 10 (±1) | 14 (±1) | 21 (±1) | 27 (±1) | 28 (±1) |
| CRC phone call | | X | | | | | | | X | |
| CRC visit | X | | X | X | X | X | X | X | | X |
| Serum CA test | X | | X | X | X | X | X | X | | X |
| Serum Albumin test | X | | X | X | X | X | X | X | | X |
| Serum P test | X | | X | X | X | X | X | X | | X |
| 24 h urine collection: Ca test | X | | | | | | | | | X |
| 24 h urine collection: Creatinine test | X | | | | | | | | | X |
| 24 h urine collection: P test | X | | | | | | | | | X |
| Pregnancy test** | X | | | | | | | | | |
| Food and medication diary | X | | | | | | | | | |
| Symptoms and signs related with abnormal serum Ca levels: questionnaire | | | | | X | | X | X | | X |
| IP supply | | | X | | | | X | | | |
| Adverse event | | | | | | | Ongoing | | | |

*Patients are informed about their eligibility to participate in the study
**For women of childbearing age Phase II

TABLE 5

Phase II procedure schedule.

| Assessment/Evaluation | -21 ±21 | *-2 ±2 | 0 ±1 | 3 ±1 | 7 ±1 | 10 ±1 | 14 ±1 | 21 ±1 | 34 ±1 | 35 ±1 | 38 ±1 | 42 ±1 | 45 ±1 | 49 ±1 | 56 ±1 | 69 ±1 | 70 ±1 |
|---|---|---|---|---|---|---|---|---|---|---|---|---|---|---|---|---|---|
| CRC phone call | | X | | | | | | | | X | | | | | | X | |
| CRC visit | X | | X | X | X | X | X | X | | X | X | X | X | X | X | | X |
| Serum CA test | X | | X | X | X | X | X | X | | X | X | X | X | X | X | | X |
| Serum Albumin test | X | | X | X | X | X | X | X | | X | X | X | X | X | X | | X |
| Serum P test | X | | X | X | X | X | X | X | | X | X | X | X | X | X | | X |
| 24 h urine collection: Ca test | X | | | | | | | | | X | | | | | | | X |
| 24 h urine collection: Creatinine test | X | | | | | | | | | X | | | | | | | X |
| 24 h urine collection: P test | X | | | | | | | | | X | | | | | | | X |
| Pregnancy test** | X | | | | | | | | | | | | | | | | |
| Food and medication diary | X | | | | | | | | | | | | | | | | |
| Symptoms and signs related with abnormal serum Ca levels: questionnaire | | | | | X | | X | X | | X | | X | | X | X | | X |
| IP supply | | | X | | | | | | | X | | | | | | | |
| Adverse event | | | | | | | | | | Ongoing | | | | | | | |

*Patients are informed about their eligibility to participate in the study.
**For women of childbearing age Pre-study (Screening) Procedures The following screening assessments are performed at screening for each subject:
  Sign an inform consent form
  Subject Medical history
  Subject current medication
  Subject Interviews
  Pregnancy test (for women of childbearing age)
  Food and medication diary for 3 consecutive days
  Compliance with inclusion/exclusion criteria
Pre-dose Procedures The following assessments are performed for each subject:
  Subject blood test for calculation of serum CA value, P and albumin
  24 hours urine collection for calcium, P and creatinine
Study Tests
Blood Tests Blood tests are performed for each subject in each CRC visit from day 0 and onward: Phase I: Day 0, 3, 7, 10, 14, 21, 28.

Phase II: Day 0, 3, 7, 10, 14, 21, 35, 38, 42, 45, 49, 56, 70.

24 Hour Urine Collection Tests
24 hour urine collection test is performed at:
  Phase I: Termination of study (Day 28)
  Phase II: Day 35 and termination of study (Day 70)
Symptoms and Signs Related with Hypocalcemia A list of questions aimed to identify symptoms and signed related with hypocalcemia is asked during the following CRC visits:
  Phase I: Day 7, 14, 21, 28
  Phase II: Day 7, 14, 21, 35, 42, 49, 56, 70
Study Measures
Blood Tests—Albumin Corrected Calcium (Ca) Calculation, Phosphorus and Albumin Serum Levels
Calcium and Albumin:

The initial assessment of hypocalcemia is usually based on the measurement of serum total calcium corrected for albumin concentration. Normal CA values range from 8.5 to 10.2 mg/dL. In subjects with hypoparathyroidism, the desired target CA values are 7.0-10.0 mg/dL.

The relationship between total serum calcium and albumin is defined by the following rule: the serum total calcium concentration falls by 0.8 mg/dL for every 1-g/dL fall in serum albumin concentration. This rule assumes that normal albumin equals 4.0 g/dL and normal calcium is 10.0 mg/dL.

Calculation: Calcium(corrected, mmol/L)=Calcium (measured, mmol/L)+{(40−albumin(g/L))×0.02}

Phosphorus (P):

The serum phosphorus test measures the amount of phosphate in the blood. Normal values range from 2.4-4.1 mg/dL.

24 Hour Urine Collection Tests

For a 24-hour urine collection, all of the urine over a 24-hour time period must be collected. The urine sample must include the last urine, 24 hours after starting the collection.

Calcium:

Test results may reflect dietary intake:

TABLE 6

| Calcium in urine | | |
|---|---|---|
| Low amount of calcium in diet: | 50-150 milligrams (mg)/24-hour sample | 1.25-3.75 millimoles (mmol) per day |
| Average amount of calcium in diet: | 100-250 mg/24-hour sample | 2.5-7.5 mmol per day |
| High amount of calcium in diet: | 250-300 mg/24-hour sample | 6.2-7.5 mmol per day |

Urine calcium level >300 mg/24 hours or >4 mg/kg of weight/24 hours is considered as hypercalciuria.

Creatinine:

A creatinine clearance test is done on a sample of urine collected over 24 hours. It is used to determine glomerular filtration rate, which helps to measure how well the kidney functions.

TABLE 7

Creatinine in urine

| | |
|---|---|
| Creatinine clearance: | Men (younger than 40 years): 107-139 milliliters per minute (mL/min) or 1.8-2.3 milliliters per second (mL/sec) Women (younger than 40 years): 87-107 mL/min or 1.5-1.8 mL/sec Creatinine clearance values normally go down with age (normal values go down by 6.5 mL/min for every 10 years past the age of 20). |

* The normal adult urine calcium/creatinine ratio is <220 mg/g.

Phosphorus:

The phosphate urine test measures the amount of phosphate in a sample of urine collected over 24 hours (24-hour urine test). Phosphate is a charged ion that contains the mineral phosphorus.

TABLE 8

Phosphate in urine

| | | |
|---|---|---|
| Adults: | 0.4-1.3 grams (g) per 24-hour urine sample | 13-42 millimoles (mmol) per day |
| Calcium- and phosphate-restricted diet: | Less than 1.0 g per 24-hour urine sample | Less than 32 mmol per day |

Results of a test to measure phosphate in urine are seldom useful on their own. They should always be interpreted along with the results of other tests. Calcium and phosphate levels are often measured at the same time.

Assessment of Symptom and Signs Related with Hypocalcemia

Subjects are asked to answer questions for the presence of symptoms and signs related with hypocalcemia (tetany, facial grimacing, paresthesias, muscle aches, arrhythmia, and depression).

Subjects' answers are documented in the CRF.

Safety of Treatment

Calcium, P and Albumin Serum Levels

Normal CA values range from 8.5 to 10.2 mg/dL. In subjects with hypoparathyroidism, the desired target CA values are 7.0-10.0 mg/dL. The initial assessment of hypocalcemia is usually based on the measurement of serum total calcium corrected for albumin concentration, according to the following formula: Calcium (corrected, mmol/L)= Calcium (measured, mmol/L)+{(40−albumin(g/L))×0.02}.

The serum phosphorus test measures the amount of phosphate in the blood. Normal values range from 2.4-4.1 mg/dL.

Urine Calcium, P and Creatinine Tests

Urine calcium level >300 mg/24 hours or >4 mg/kg of weight/24 hours is considered as hypercalciuria.

Normal Urine creatinine levels in men (younger than 40 years) are 107-139 milliliters per minute (mL/min) or 1.8-2.3 milliliters per second (mL/sec) and in women (younger than 40 years) are 87-107 mL/min or 1.5-1.8 mL/sec. Creatinine clearance values normally go down with age (normal values go down by 6.5 mL/min for every 10 years past the age of 20).

Urine calcium measurement is expressed in relation to creatinine

A normal reference interval for the urine calcium (mg/dL): urine creatinine (mg/dL) ratio is <0.14.

Normal phosphate levels are 0.4-1.3 grams (g) per 24-hour urine sample.

Complications

Symptoms and signs related with hypocalcemia (tetany, facial grimacing, paresthesias, muscle aches, arrhythmia, depression) are documents.

Statistical Analysis

This is a two-stage prospective study in which ACC is evaluated as a replacement for CCS in subjects with hypoparathyroidism. Efficacy is evaluated by the degree to which smaller doses of ACC replacing larger doses of CCS are able to provide the supplemental calcium required by individuals with hypoparathyroidism. Safety is evaluated by adverse events (AEs) including those related to urinary calcium excretions. Statistical plan and analysis are carried out by TechnoSTAT Ltd.

Design Considerations

This is a two-phase study in which the first phase evaluates a predetermined conversion factor from CCS to ACC in subjects with hypoparathyroidism. During this phase progressively larger proportions of CCS are replaced with ACC depending on subject response, hence the adaptive nature of this phase.

If the first phase of the trial demonstrates the safety of the conversion factor, the second phase is initiated. The second phase comprises a crossover trial with newly recruited subjects; i.e. subjects who did not participate in the first phase of the trial. Each of these subjects is block randomized in 1:1 ratio to CCS Control or ACC Treatment. In the second leg of the crossover each subject receives the alternative formulation which he or she did not receive in the first leg.

The study duration per subject participating in phase I is 49 days from screening (day −21) until termination (day 28) and 91 days from screening (day −21) until termination (day 70) per subject participating in phase II.

Visits to the CRC takes place on days 0 (baseline), 3, 7, 10, 14, 21 and 28 (end-of-phase I) and on days 0 (baseline), 3, 7, 10, 14, 21, 35, 38, 42, 45, 49 and 70 (end-of-phase II) for phase I and phase II, respectively.

Blood and urine tests and clinical questionnaire are performed during subjects' visits at the clinic.

Analysis Sets

Safety Population

The safety population consists of all patients in both study stages for whom ACC or CCC were administered as part of trial procedures.

Efficacy Population

The efficacy population consists of Phase II subjects with no major entry violations likely to affect outcome, for whom there are baseline and at least some post-treatment data on serum CA levels. The degree to which an entry violation is likely to affect outcome is determined by a reviewer blind to outcome (i.e. blind review).

Treatment of missing values: only observed data is used; missing data is not imputed.

Endpoints

Safety

Overall incidence of product related adverse events.

All adverse events and serious adverse events are collected and reported.

Primary Efficacy

In Phase I: Change in elemental calcium doses from ACC achieving normalization in serum CA and urine calcium levels In Phase II: Serum CA and urine calcium levels Secondary Efficacy
  Secondary efficacy endpoints include:
   Side effects associated with calcium levels
   Symptoms related to hypocalcemia
   Serum phosphorous levels
Data Analysis
Overview Safety and subject disposition analyses are conducted on the safety population. Efficacy analyses are done on the efficacy population. Phase I and II results are analysed and presented separately.

The data is summarized in tables listing the mean, standard deviation median, minimum, maximum and number of subjects for continuous data, or in tables listing count and percentage for categorical data where appropriate. Tables are presented by study arm, over time and overall. In Phase I, study arms consist of ACC intake before or after meals. In Phase II, study arms consist of CCS or ACC.

All statistical analyses are performed and data appendixes are created using the SAS® system. The effects of noncompliance, dropouts, and possible covariates such as Age and Gender are assessed to determine the impact on the general applicability of results from this study.

Subject Disposition

Subject disposition is tabulated; the number of enrolled, exposed, prematurely terminated and completed subjects is summarized.

A list of dropouts is prepared including reason for discontinuation, and time of discontinuation.

Safety

The safety analyses are descriptive and narrative in nature, with SAE's and AE's coded using MedDRA and tabulated by body system, preferred term, study arm, severity and relation to procedure. Descriptive statistics and shift analysis tables, indicating changes between "normal" and "abnormal" values, are provided as appropriate for laboratory tests.

Primary Efficacy Analyses: Phase I

Phase I data is summarized numerically and graphically, showing for each subject, by arm and overall the relationship between calcium levels by amount of ACC replacement of CCS received. ACC and serum CA levels are described over time for each individual, by arm and overall, numerically, by shift tables and graphically.

Primary Efficacy Analyses: Phase II

Serum CA levels are summarized both numerically and graphically by arm over time and for differences between arms over time for parallel, paired time points (D0,D35; D3,D38; D7,D42; D10,D45; D14,D49; D21, D56). Differences in CA levels between arms at parallel time points are compared by paired t-test or Wicoxon Sign-rank test depending on the distribution of differences.

Secondary Analyses

Side effects associated with a change is serum calcium levels as well as symptoms related to hypocalcemia are described by arm in both Phase I and Phase II. Serum phosphorous levels are described by arm over time in Phase I and Phase II, as well as by differences between arms at parallel time points in Phase II. Shift tables are provided by arm for both Phases.

Interim Analysis

There is no formally planned interim analysis within either of the two study phases. However, safety data, which includes serum CA and phosphorous levels, is monitored continuously.

Phase I results are examined before deciding whether or not to embark on the crossover portion of the study planned for Phase II.

Data Management

Investigational data is recorded on paper CRFs. CRFs are filled for enrolled subjects only (not screening failures). Through his/her signature on the CRF, the investigator certifies that the data collected for each patient are accurate, complete and legible.

All data generated in the current clinical investigation are managed according to TechnoSTAT standard procedures. Data and other study documentation are archived for a minimum of 6 years after the completion of the investigation.

Safety
Definition of Adverse Events

An adverse event is any untoward medical sign (including an abnormal laboratory finding), symptom or disease temporally associated with the use of the IPs whether or not considered as IP related. A new condition or the worsening of a pre-existing condition is considered an AE. All abnormal findings considered to be clinically significant must be recorded as adverse events.

The cases of acute medical situation (which are assessed within 48 hours from the beginning of the study) that are considered significant by the Principal Investigator (such as pins and needles, numbness around the mouth, cramps, anxiety, muscular contractions, seizures, stridor, psychosis, nausea, vomiting, loss of appetite, constipation, stomach pain, thirst, dry mouth and increased urination) are documented in the Case Report Form (CRF) and the subject is excluded from the experiment.

In all cases, the etiology of the AE should, as much as possible, be identified and the Sponsor notified by recording in the CRF.

The relationship of the adverse event to the IP is defined as follows:

TABLE 9

The relationship of the adverse event to the IP

| | |
|---|---|
| Most probably related: | Follows a reasonable temporal sequence from study IP administration and cannot be reasonably explained by known characteristics of the patient's clinical data |
| Possibly related: | Follows a reasonable temporal sequence from study IP administration but could have been produced by the patient's clinical state |
| Probably not related: | Temporal association is such that the study IP is not likely to have had any reasonable association with the observed event. |
| Not related: | No relationship to study IP is perceived. |

Serious adverse event (SAE) is any adverse event that:
  Led to death.
  Resulted in a life-threatening illness or injury.
  Resulted in permanent impairment of a body structure or body function
  Required inpatient hospitalization or prolongation of existing hospitalization.
  Resulted in medical or surgical intervention to prevent permanent impairment to body structure or body function
  Led to fetal distress, fetal death, congenital abnormality or birth defect.

Definitions of Adverse Event Intensity

The following definitions should be used by the investigating physician to describe the intensity of adverse events.

The following are the only definitions which should be used to describe adverse event intensity. Only one severity definition should be used for each adverse event (e.g. "mild-moderate" is not acceptable).

TABLE 10

Adverse Event intensity

| Intensity | Definition |
|---|---|
| Mild | Adverse experience which is easily tolerated |
| Moderate | Adverse experience sufficiently discomforting to interfere with daily activity. |
| Severe | Adverse experience which prevents normal daily activities. |

Abnormal Laboratory Values

A clinical laboratory abnormality is documented if any one of the following conditions is met:
  The laboratory abnormality is present in a repeated test
  The abnormality is of a degree that requires active management (e.g. change of dose, discontinuation of the treatment, more frequent follow-up assessments, etc.).
  Normal laboratory values are:
  Serum calcium (albumin corrected): 7.0 to 10.0 mg/dL
  Serum phosphorus: 2.4-4.1 mg/dL
  Urine calcium: >300 mg/24 hours
  Urine creatinine 40 to 300 mg/dl
  Urine phosphate: 0.4-1.3 grams (g)
  Abnormal laboratory results that are not within the normal reference range are recorded and treated.

Recording of Adverse Events

All of the following details should be recorded in the subject's CRF for each adverse event:
  Full description of adverse event.
  Date and time of onset.
  Date and time of resolution.
  Severity of event, to be assessed by the investigating physician in accordance with the definitions in Section 16.2.
  Relationship to study IPs is assessed by the investigating physician.
  Action taken (if any).
  Outcome and details of any further follow-up.

Anticipated Side Effects (Adverse Events)

The following is a list of ACC investigational product possible adverse events. The list is based on prior experience from use of natural ACC and effects related to crystalline forms of calcium consumption:
  Belching
  Gas
  Constipation
  Nausea
  Vomiting
  Loss of appetite
  Increased urination
  Kidney damage
  Confusion
  Irregular heart rhythm.

Trial 3: Calcium Bone Absorption in Corticosteroids Consuming Individuals

The experiment aiming to evaluate the bioavailability of the calcium source comprising stable Amorphous Calcium Carbonate (ACC) for bone mineralization in the subjects suffering from calcium malabsorption associated diseases, disorders and conditions is conducted. A multicenter prospective, randomized, parallel, double-blind, active controlled study is performed, comparing the effect of amorphous calcium carbonate (ACC) versus crystalline calcium carbonate (CCC) on bone mineral density of patients chronically treated with corticosteroids The primary objective of the trial is to assess the efficacy of treatment with calcium from ACC compared to CCC on preservation of bone mineral density in patients exposed to long-term treatment of corticosteroids. The secondary objective is to evaluate the effect of ACC compared to CCC on fractures' prevalence during the study period. The further secondary objective is to evaluate the effect of ACC compared to CCC on bone metabolism biomarkers. The yet further objective of the trial is to evaluate the safety profile of ACC in this population.

Selection of Study Population

The study population includes sixty (60) subjects taking continuous long-term corticosteroid therapy, thirty (30) subjects in each treatment group.

Description of the Investigational Product

The stable amorphous calcium carbonate used in the study is a synthetic ACC stabilized by low concentrations of phosphoserine and citrate (less than 0.5% in the final product), provided by Amorphical Ltd, as disclosed hereinabove.

Description of the Control Product

The control product contained in each capsule 500 mg of crystalline calcium carbonate (200±5 mg elemental calcium) and 167 mg of sucrose. Elemental calcium level in the control product was equal to the elemental calcium level in the treatment group in order to evaluate the effect of amorphous calcium carbonate compared to crystalline calcium carbonate.

Dosage and Administration

Eligible subjects have randomly received one of the two treatments. Each dose of the study supplement consisted of 667 mg of ACC or 500 mg CCC in each capsule.

TABLE 11

Dose of Study Treatment

| Group | Treatment |
|---|---|
| Investigational Product | Tablets for oral use containing 667 mg ACC (200 mg elemental calcium) |
| Control Product | Tablets for oral use containing 500 mg CCC (200 mg elemental calcium) and 167 mg of sucrose. |

Selection of the dosage is based on the recommended daily intake of elemental calcium for subjects of age 19-50 (1000 mg/day). The calcium dosage in the control is equaled to the elemental calcium levels in ACC product.

Allocation of Subjects to Treatment

Subjects are assigned to one of the treatment groups randomly according to a randomization list. Randomization to each of the two study arms is performed using block randomization within center.

Blinding

The oral calcium treatments administered in the clinical trial are blinded. The subjects, the investigators and any personnel involved in subjects' assessment, monitoring, analysis and data management are blinded to the subject formulation assignment, except the Sponsor who is responsible for preparing, dispensing and labeling the investigational product. Blinded labels are affixed to the vials prior to dosing by the un-blinded Sponsor.

Randomization Procedures

The study is double blinded and therefore the CRC staff and the subject remain blinded to the code assignments throughout the study. Prior to administration, each subject is assigned with an individual number and is treated according to the predetermined computer generated randomization list. A computer-generated algorithm is used to assign the subject into the treatment groups. The treatment compositions are prepared by the Sponsor and labels are affixed to the vials prior to shipping. The hospital pharmacists are instructed to dispense the products to the CRC according to the cohort assignment lists.

Study Design

Sixty (60) patients that are currently beginning long-term (≥6 months) glucocorticosteroid treatment are randomly assigned to one of two groups (N=30). Patients in the treatment group receive amorphous calcium carbonate (ACC) and those in the active control group receive crystalline calcium carbonate (CCC). Both formulations are supplemented with vitamin D upon need, based on the doctor's decision. Safety parameters are evaluated throughout the trial.

Patients admitting to the CRC due to various medical conditions are routinely evaluated. Subjects that are beginning a long-term treatment with glucocorticosteroids due to their medical condition are considered candidates for the trial and are invited to the CRC for screening.

Screening (Day −7)—Subjects sign an informed consent form (ICF). Chemistry and hematology tests are performed: sodium, potassium, hemoglobin, sedimentation rate, leukocytes calcium (total, albumin-corrected), phosphate, alkaline phosphatase, creatinine, and albumin are measured. Also, serum PTH, 25-hydroxyvitamin D, and thyroid-stimulating hormone (TSH) are tested. Urinary excretion of calcium and creatinine are measured. General health is examined by medical history and physical examinations. Eligible subjects, complying with all inclusion criteria and none of the exclusion criteria are enrolled to the study.

Subjects are informed by phone or on site whether they are eligible to enter the study.

Visit 1 (Day 0)—Eligible subjects are invited to the CRC. DEXA scan is performed at baseline. BMDs are measured for the lumbar spine (L2-4), femoral neck and whole body. Evidences for existing fractures are documented. Serum levels of albumin, calcium (Ca), phosphorus, and creatinine (Cr), as well as urinary Ca and Cr are measured. Biochemical markers of bone metabolism (serum osteocalcin (OCN), P1NP (total procollagen type 1 N-terminal propeptice), bone-type alkaline phosphatase (BAP) and urinary levels of type I collagen cross-linked N-telopeptide (NTX)) are measured. Subjects randomly receive packs of tablets, each capsule containing 200 mg elemental calcium (210 tablets for 42 day supply+20 spare tablets, a total of 230 tablets) with one of the formulations (ACC or CCC). Subjects are instructed to take 5 capsules a day for the first 6 weeks (days 0-42), 2 tablets in the morning and 3 tablets in the evening, after a meal. To minimize the risks for calcium related side effects, subjects who take calcium regularly, are instructed to discontinue their calcium supplements intake throughout the trial. Subjects are advised to take vitamin D3 supplementation based on the doctors' decision. Subjects are asked to keep a daily diary to record their glucocorticoid use.

Visit 2 (Day 42±3)—Subjects are asked about any side effects or AEs that may have occurred. Subjects are asked about any fracture event that occurred since their last visit to the CRC. Subjects complete the TSQM questionnaire with the representative of the CRC. Subjects receive additional packs of tablets, each tablets containing 200 mg elemental calcium (a total of 210 tablets, 42 day supply+20 spare tablets) of the same formulation (ACC or CCC) that has been received in the previous visit. Subjects are reminded to take 5 tablets a day for the next 6 weeks (days 42-84), 2 tablets in the morning and 3 tablets in the evening, after a meal. To minimize the risks for calcium related side effects, subjects who take calcium regularly, are reminded to discontinue their calcium supplements intake throughout the trial. Subjects are advised to take vitamin D3 supplementation based on the doctors' decision. Subjects are asked to keep a daily diary to record their glucocorticoid use.

Visit 3—(Day 84±3)—DEXA scan is performed. BMDs are measured for the lumbar spine (L2-4), femoral neck and whole body. Pre-dose Serum levels of albumin, calcium (Ca), phosphorus, and creatinine (Cr), as well as urinary Ca and Cr are measured. Biochemical markers of bone metabolism are measured as well. Subjects are asked about any side effects or AEs that may have occurred. Subjects are asked about any fracture event that occurred since their last visit to the CRC. Subjects receive additional packs of tablets, each containing 200 mg elemental calcium (a total of 210 capsules, 42 day supply+20 spare tablets) with the same formulation received in day 0. Subjects are instructed to take 5 tablets a day for the next 6 weeks (days 84-126) 2 tablets in the morning and 3 tablets in the evening, after a meal. To minimize the risks for calcium related side effects, subjects who take calcium regularly, are reminded to discontinue their calcium supplements intake throughout the trial. Subjects are advised to take vitamin D3 supplementation based on the doctors' decision. Subjects are asked to keep a daily diary to record their glucocorticoid use.

Visit 4—(Day 126±3)—Subjects are asked about any side effects or AEs that may have occurred. Subjects are asked about any fracture event that occurred since their last visit to the CRC. Subjects receive additional packs of tablets, each capsule containing 200 mg elemental calcium (a total of 210 tablets, 42 day supply+12 spare tablets) of the same formulation (ACC or CCC) that has been received in the previous visit. Subjects are reminded to take 5 tablets a day for the next 6 weeks (days 126-168), 2 tablets in the morning and 3 tablets in the evening, after a meal. To minimize the risks for calcium related side effects, subjects who take calcium regularly, are reminded to discontinue their calcium supplements intake throughout the trial. Subjects are advised to take vitamin D3 supplementation based on the doctors' decision. Subjects are asked to keep a daily diary to record their glucocorticoid use and to bring it with them to the next visit.

Visit 5—(Day 168±1)—DEXA scan is performed. BMDs are measured for the lumbar spine (L2-4), femoral neck and whole body. Pre-dose serum levels of albumin, calcium (Ca), phosphorus, and creatinine (Cr), as well as urinary Ca and Cr are measured. Biochemical markers of bone metabolism are measured as well. Subjects are asked about any fracture event that has occurred since their last visit to the CRC. Subjects complete the TSQM questionnaire with the representative of the CRC. Subjects are asked about any side effects or AEs that may have occurred.

Outcome Measures

Preservation of Bone Mineral Density (BMD)—BMD is defined by Dual Energy X-ray Absorptiometry (DEXA) scan. The DEXA results are presented as Z-score (comparing the results of a specific scan to other people at the same age, weight, ethnicity, and gender). A Z-score of less than −1.5 raises concern of factors other than aging as contributing to bone loss.

Fracture prevalence—fracture events are documented in each visit.

Increase in bone formation markers

Reduction in bone resorption markers

Assessment of calcium side effects:

Safety Analysis

The safety analyses are descriptive and narrative in nature. The safety endpoints are adverse events (AEs) and serious AEs (SAES) whether or not related to study treatment. Also included are serum calcium levels and urine calcium and creatinine levels.

Efficacy Analysis

The primary efficacy endpoint is preservation of BMD, by Z-values calculated by DEXA scan. Hypotheses are tested by independent groups t-test on raw values if these are distributed approximately normal. Log-transform is used to normalize the data, if the data substantially deviates from normal. If after applying the latter the data still deviates from normal, the non-parametric Wilcoxon Rank-sum test is used. The trial is considered successful, if the Z-score is significantly smaller in Treatment relative to Control.

The following are the study's secondary efficacy endpoints:
  Reduction in fractures' frequency
  TSQM (Treatment Satisfaction Questionnaire for Medication) domains: A 14-item psychometrically robust and validated questionnaire consisting of four scales: the effectiveness scale, the side effects scale, the convenience and the global satisfaction scale.

Trial 4: Calcium Gastrointestinal Absorption in Populations Susceptible to the Development of Osteoporosis.

The objective of the present study was to evaluate the gastrointestinal absorption of calcium from the ACC source in population susceptible to the development of bone loss related disorders. The trial is a clinical study that used the dual-stable calcium isotopes technique performed on postmenopausal women.

Ten postmenopausal women (demographic data in Table 12), with no more than 5 years from menopause were included in the study. All subjects, exhibiting BMI of 18-29, were apparently healthy and did not suffer from any major medical illness or metabolic bone disorder. Exclusion criteria included women who, on the basis of a food diary consumption, have an estimated daily calcium intake >1100 mg through combined diet (from both supplements and food), vitamin D deficiency exhibited by values <20 ng/ml in the serum, hypercalcemia, nephrolithiasis, inflammatory bowel disease, malabsorption, chronic diarrhea, use of antibiotics within the past month and women suffering from digestive, hepatic, renal, or inflammatory diseases. Women who take oral steroids, anticonvulsants, bisphosphonates, estrogen compounds, calcitonin, or teriparatide within the past 6 months were also excluded from the study. Written informed consent was obtained from each woman after approval of the protocol by the Ethical Committee of Sourasky Medical Center, Tel-Aviv, Israel.

TABLE 12

Demographic data of 10 women that participated in the study

| Variable | |
|---|---|
| Age, y | 55 ± 3.2 |
| Height, cm | 159.3 ± 3.7 |
| Weight, kg | 66.8 ± 5.1 |
| BMI, kg/cm$^2$ | 26.2 ± 1.9 |
| PTH, pg/ml | 30.3 ± 13.2 |
| FSH, miu/ml | 65.2 ± 29.3 |
| 25-OHD, ng/ml | 29.9 ± 6.7 |

Results are means ± S.D

Fractional absorption analysis revealed that all 10 subjects showed a significant elevation in calcium absorption when being administered ACC instead of CCC.

Figure 2:
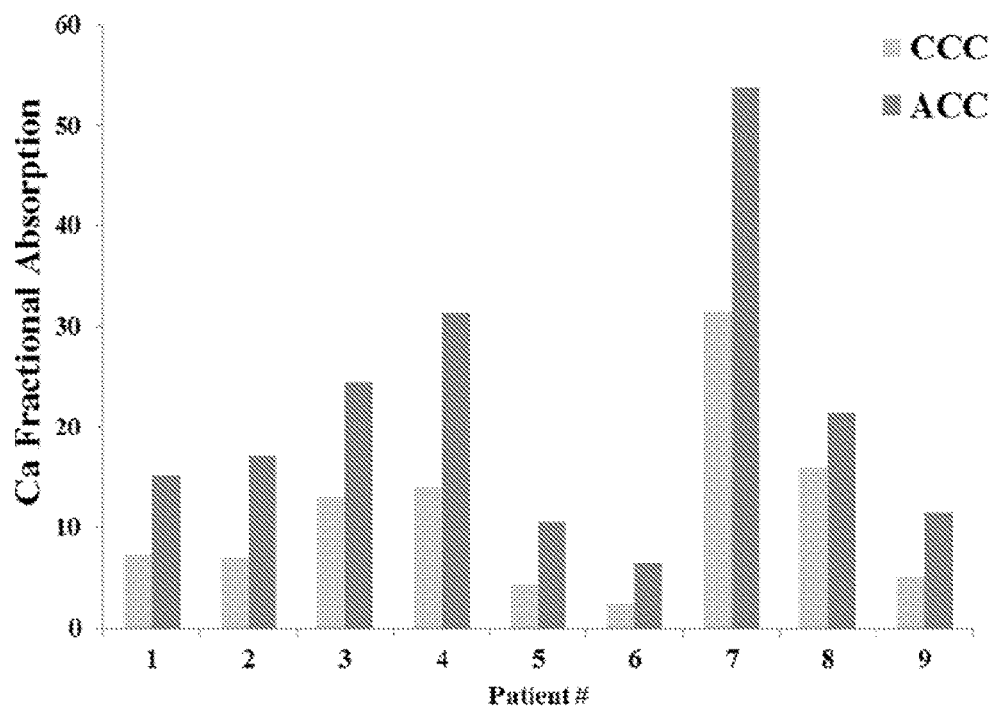
FIG. 2: Calcium fractional absorption is increased by 2.1 fold per each woman following amorphous calcium carbonate administration (ACC) vs. crystalline calcium carbonate (CCC) in fed postmenopausal women Paired t-Test: $p<0.01$

Paired t-test analysis of the results obtained from 9 women that received the capsules after breakfast showed a significant elevation of fractional calcium absorption for ACC. The average increase in the relative absorption of calcium from ACC vs. CCC for each woman was 2.1 fold (p<0.01; FIG. 2).

Figure 3:
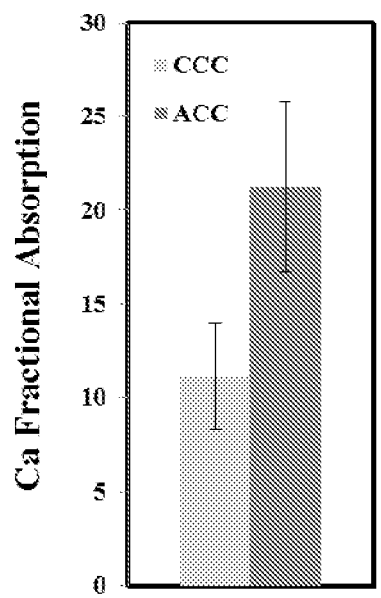
FIG. 3: Calcium fractional absorption is increased by 1.9 fold as two separated groups analyzed following amorphous calcium carbonate administration (ACC) vs. crystalline calcium carbonate (CCC) in fed postmenopausal women Results are Means±SEM Student's t-Test: *$p<0.05$

Overall as two separated treatment groups, there was a 1.9 elevation in calcium fractional absorption when women were administered with ACC compared to CCC (p<0.05; FIG. 3).

Figure 4:
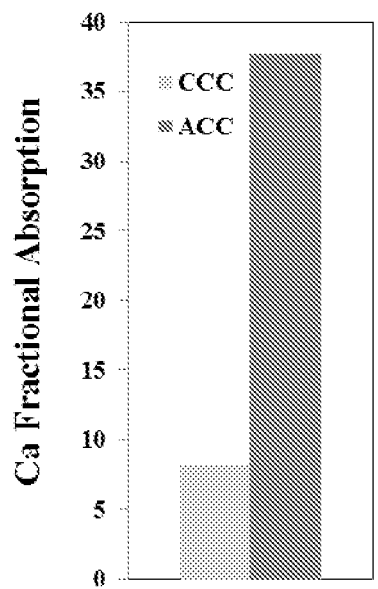
FIG. 4: Calcium fractional absorption is increased by 4.6 following amorphous calcium carbonate administration (ACC) vs. crystalline calcium carbonate (CCC) in one fasted postmenopausal woman

One out of the ten women who received the capsules on an empty stomach after an overnight fast presented a 4.6 fold elevation in calcium fractional absorption (FIG. 4).

Experimental Details

Capsules and CaCl$_2$ Solution Preparation and Labeling

ACC (Amorphical Ltd.) was intrinsically labeled by dissolving appropriate amount of it in 32% HCl together with $^{44}$CaCO$_3$ (enriched to 96.1%, CMR, Moscow, Russia), after which it was reprecipitated back to ACC powder containing 192 mg elemental calcium (600 mg powder) labeled with 15 mg $^{44}$Ca per treatment. Overall, 3 batches of $^{44}$ACC were prepared and sent to magnetic sector thermal ionization spectrometry (MAT 261; Finnigan, Bremen, Germany) for 44:42 molar ratio analysis, and to calcium content measurement by atomic absorption (Analytical Research Services, Ben-Gurion University, Beersheva, Israel). Additional tests evaluating the amorphous content for each batch were performed: X-ray diffraction (XRD; The Nanotechnology Institution, Ben-Gurion University), quantitative polarized spectroscopy (QPS), polarized optical microscopy (POM) and dryness. CCC (Zifroni Chemicals Suppliers Ltd., Rishon-Lezion, Israel) was intrinsically labeled by homogenizing appropriate amount of it with $^{44}$CaCO$_3$ (enriched to 96%, CMR, Moscow, Russia) to reach CCC powder containing 192 mg elemental calcium (480 mg powder) labeled with 15 mg $^{44}$Ca per treatment. To match the volume in the ACC capsules, sucrose (120 mg per treatment; FAGRON Gmbh & Co. KG, Rotterdam, The Netherlands) was added to each capsule. One batch of $^{44}$CCC was prepared and sent to magnetic sector thermal ionization spectrometry (MAT 261; Finnigan, Bremen, Germany) for 44:42 molar ratio analyses.

Isotopic i.v. $^{42}$CaCl$_2$ solution preparation procedures were conducted by Concept for Pharmacy Ltd. Kfar-Saba, Israel under the laminar flow hood to ensure sterility. The appropriate amount of $^{42}$CaCO$_3$ (enriched to 96.3%, CMR, Moscow, Russia) was dissolved in 37% HCl and mixed with 0.45% NaCl. The pH was adjusted with 10N NaOH to 5.5. The solution was forced through a 0.22µ sterilization filter into a sterile container. Individual doses (1.5 mg $^{42}$Ca/dose) were transferred into sterile vials for later use. Aliquots were sent for sterility and pyrogenicity testing (Aminolab, Nes-Ziona, Israel) and for calcium content measurement by atomic absorption (Analytical Research Services, Ben-Gurion University, Beersheva, Israel) before use. All of i.v. solutions in the study were sterile and free of pyrogens.

Urine Collection and Analysis

Following each capsules administration, a timed 24-hour urine collection was performed for measurements of calcium, sodium, potassium, urea, creatinine and stable isotope analysis. Calcium absorption analyses were performed at Baylor College of Medicine Houston, Tex., USA, following previously published methods (Yergey et al 1994). Ammonium oxalate was used to precipitate calcium isotopes in the urine samples (Yergey et al 1980). The amount of extracted calcium was then used for calcium isotope ratio measurements. This amount was determined using magnetic sector thermal ionization spectrometry (MAT 261; Finnigan, Bremen, Germany).

Pharmacokinetic Calculations of Human Samples

Fractional absorption ($\alpha_{24h}$) of dietary calcium was calculated as described in (Yergey et al 1994). In brief, the ratio $\alpha_{24h}$ is an arithmetically valid representation of the ratio of the areas under the plasma disappearance curves for the two labels.

Statistical Analysis

The statistical analysis of variance was performed as described in trial 1.

The results of the above trial confirmed that stable ACC has higher gastrointestinal absorption than CCC both in human models, susceptible to the development of bone related disorders. Such enhanced absorption may be beneficial in cases when higher calcium intake in required for maintaining bone mineral density, as the absorption of crystalline calcium is limited and the excess of calcium may lead to adverse effects.

Trial 5: Preventing or Delaying Bone Loss in Bone Mineral Density Loss Associated Disorders.

The objective of the present trial was to evaluate availability of calcium from the ACC source comprising various stabilizers (P-Ser, citric acid or sucrose), for bone mineralization process assessed by femoral and vertebral bone mineral density (BMD) in osteoporosis rat model (ovariectomy; OVX).

In the study, four groups of rats were tested (3 ovariectomized and 1 sham). The animals were treated according to Table 13.

Table 14 presents the mean food consumption and body weight of the rats during the trial. A significant weight increase was observed in the three OVX groups compared to sham. This is despite the fact that food consumption was lower among all OVX groups compared to the sham group.

TABLE 13

Assignment of rats according to the treatment

| Group | Treatment |
|---|---|
| Sham (n = 10) | Standard laboratory diet containing 1% elemental calcium (Altromin Spezialfutter GmbH & Co, #1320P Seelenkamp, Germany) ad libitum. |
| OVX ACC (P-Ser) (n = 10) | Low calcium diet (TD.95027, Harlan Inc, Jerusalem, Israel) enriched with 1% elemental calcium from synthetic ACC stabilized by 0.0275% phosphoserine (ACC_PS, SOP PSC002, Amorphical Ltd.) ad libitum. |
| OVX ACC (CIT) (n = 10) | Low calcium diet (TD.95027, Harlan Inc, Jerusalem, Israel) enriched with 1% elemental calcium from synthetic ACC stabilized by 0.0275% citric acid (ACC_CIT, SOP PCA001, Amorphical Ltd.) ad libitum. |
| OVX ACC (SUC) (n = 10) | Low calcium diet (TD.95027, Harlan Inc, Jerusalem, Israel) enriched with 1% elemental calcium from synthetic ACC stabilized by sucrose and sodium hydroxide (ACC SUC, SOP SUC001, Amorphical Ltd.) ad libitum. |

OVX = ovariectomy; ACC = amorphous calcium carbonate; PS = phosphoserine'; CIT = citrate; SUC = sucrose

TABLE 14

Mean food consumption and total body weight of the rats at the beginning and at the end of the experiment

| | Sham | OVX | | |
|---|---|---|---|---|
| | | ACC_P-Ser | ACC_CIT | ACC_SUC |
| Rat body weight (Day 0) | 258 (16) | 245 (15) | 244 (11) | 255 (14) |
| Rat body weight (Day 90) | 299 (29) | 337 (18) | 341 (16) | 357 (22) |
| *Weight gain (%) | 23.7$^a$ | 36.1$^b$ | 41.2$^b$ | 40.7$^b$ |
| *Mean food consumption | 17.2 (1.0)$^a$ | 14.0 (0.8)$^b$ | 14.5 (0.5)$^{bc}$ | 15.5 (0.7)$^c$ |

Values were recorded weekly. Weight gain represents the increased rate of weigh from the beginning to the end of the experiment. Values are represented as mean (SD). One-way ANOVA: p < 0.001.
Letters represents Tukey's post hoc comparison tests.

As expected in this model, micro-CT scanning of the femur of the OVX groups revealed a significant reduction in trabecular bone mineral density (Tb.BMD) and other morphometric parameters, i.e: bone volume/tissue volume (BV/TV), trabecular number (Tb.N), trabecular thickness (Tb.Th); and a significant elevation in trabecular separation (Tb.Sp). In addition, the 3 OVX groups were significantly different from the sham animals in all femoral microarchitectural topology and orientation parameters, i.e.: trabecular bone factor (TBPf), structural model index (SMI) and degree of anisotropy (DA) (Table 15).

Results of the 4-L vertebra micro-CT scan show that the sham group was significantly higher compared to all other OVX groups only in BMD, BV/TV and Tb.N parameters and significantly lower in TBPf and SMI microarchitectural parameters (Table 15).

In contrast to the trabecular BMD, no differences between all groups were observed in the cortical bone BMD (Ct. BMD) of both the femur and vertebra (Table 15).

In all parameters tested by the micro-CT, no difference was observed among the ACC+P-Ser, ACC+CIT and the ACC+SUC groups in both femur and vertebra (Table 6), indicating that the compound that stabilizes ACC by itself has no effect on BMD or additional bone morphometric or microarchitectural parameters.

TABLE 15

Morphometric and microarchitectural topology & orientation parameters studied by micro-CT

| | | Sham | OVX | | |
|---|---|---|---|---|---|
| | | | ACC + P-Ser | ACC + CIT | ACC + SUC |
| (A) Femur | *Tb. BMD, g/cm$^3$ | 305 (43)$^a$ | 120 (26)$^b$ | 112 (20)$^b$ | 116 (27)$^b$ |
| | Ct. BMD, g/cm$^3$ | 775 (79)$^a$ | 771 (32)$^a$ | 761 (84)$^a$ | 743 (55)$^a$ |
| | *Tb. BV/TV, % | 55 (7.5)$^a$ | 22 (3.7)$^b$ | 21 (3.6)$^b$ | 22 (3.6)$^b$ |
| | *Tb. N, mm$^{-1}$ | 4.5 (0.3)$^a$ | 2.0 (0.3)$^b$ | 2.0 (0.3)$^b$ | 2.1 (0.3)$^b$ |
| | *Tb. Sp, μm | 145 (15)$^a$ | 583 (67)$^b$ | 621 (125)$^b$ | 613 (92)$^b$ |

TABLE 15-continued

Morphometric and microarchitectural topology
& orientation parameters studied by micro-CT

| | | Sham | OVX ACC + P-Ser | OVX ACC + CIT | OVX ACC + SUC |
|---|---|---|---|---|---|
| (B) Vertebra | *Tb. Th, μm | 121 (1)$^a$ | 109 (6)$^b$ | 105 (6)$^b$ | 104 (6)$^b$ |
| | *TBPf, mm$^{-1}$ | −11.4 (4.0)$^a$ | 5.20 (1.6)$^b$ | 5.99 (1.7)$^b$ | 4.60 (1.7)$^b$ |
| | *SMI | −0.84 (0.8)$^a$ | 1.40 (0.1)$^b$ | 1.46 (0.2)$^b$ | 1.32 (0.2)$^b$ |
| | *DA | 1.46 (0.1)$^a$ | 1.64 (0.2)$^b$ | 1.82 (0.2)$^b$ | 1.61 (0.2)$^b$ |
| | *Tb. BMD, g/cm$^3$ | 235 (41)$^a$ | 107 (37)$^b$ | 124 (39)$^b$ | 130 (29)$^b$ |
| | Ct. BMD, g/cm$^3$ | 652 (50)$^a$ | 687 (35)$^a$ | 663 (41)$^a$ | 669 (48)$^a$ |
| | *Tb. BV/TV, % | 42 (6.6)$^a$ | 22 (5.1)$^b$ | 24 (5.4)$^b$ | 25 (5.3)$^b$ |
| | *Tb. N, mm$^{-1}$ | 3.6 (0.5)$^a$ | 2.1 (0.4)$^b$ | 2.1 (0.9)$^b$ | 2.2 (0.4)$^b$ |
| | Tb. Sp, μm | 221 (34)$^a$ | 335 (53)$^a$ | 297 (48)$^a$ | 333 (57)$^a$ |
| | Tb. Th, μm | 117 (5)$^a$ | 105 (7)$^a$ | 107 (10)$^a$ | 111 (6)$^a$ |
| | *TBPf, mm$^{-1}$ | −0.99 (3.5)$^a$ | 7.04 (2.5)$^b$ | 5.85 (2.8)$^b$ | 5.73 (1.7)$^b$ |
| | *SMI | 0.41 (0.5)$^a$ | 1.51 (0.3)$^b$ | 1.56 (0.7)$^b$ | 1.40 (0.2)$^b$ |
| | DA | 2.03 (0.3)$^a$ | 2.64 (0.7)$^a$ | 2.36 (0.4)$^a$ | 2.13 (0.4)$^a$ |

(A) Distal femur metaphysis. (B) 4$^{th}$-lumbar vertebra.
Trabecular bone mineral density (Tb. BMD), cortical BMD (Ct. BMD), Trabecular bone volume/tissue volume (Tb. BV/TV), Trabecular number (Tb. N), trabecular separation (Tb. Sp), trabecular thickness (Tb. Th), Trabecular bone pattern factor (TBPf), structure model index (SMI), degree of anisotropy (DA).
Values correspond to means (±SD).
One-way ANOVA:
*p < 0.001.
Letters represents Tukey's post-hoc comparison tests.

Experimental Details
Animals

Forty 16-17 weeks old female Sprague Dawley rats (Harlan Inc., Jerusalem, Israel) with an average body weight of 247±14 g were group-housed in 14 cages (2-3 rats/cage) and acclimated under controlled room conditions (21±2° C. and 12-hours dark-light cycle). During 7 days acclimation, rats were fed with standard laboratory diet containing 1% elemental calcium (#2018SC Rat chow, Harlan Inc. Jerusalem, Israel) and de-ionized water ad-libitum.

Following the 7 days acclimation period, rats were anesthetized using intraperitoneal (IP) injection of anesthetic solution (0.1 ml/100 g) containing Ketamine (Fort Dodge AH Ltd. Overland Park, USA) and Xylazine (EuroVet AH Ltd. Bladel, UK).

Rats were randomly assigned and operated according to their assigned four groups: Sham (sham-Ovariectomized; fed with standard laboratory diet containing 1% elemental calcium from CCC) and three other groups were ovariectomized (OVX) using a bilateral dorsal approach according to Lasota and Danowska-Klonowska (2004) Rocz Akad Med Bialymst 49 Suppl 1:129-131, and divided to OVX-ACC+PS, OVX-ACC+CIT and OVX-ACC+SUC. Following operation, rats were provided a 7 days recovery period under the same conditions as the acclimation period, standard laboratory diet ad-libitum and de-ionized water containing 1.5 ml/400 ml Dipyrone (Vitamed Ltd, Binyamina, Israel), and 1 mg/kg Enrofloxacin (Buyer Ltd. Leverkusen, Germany).

Experimental Treatment

At the end of the recovery period the rats were group-housed (2 rats/cage) according to the group assignment, under the same controlled room conditions as described above. The assigned food pellets (described in Table 13) and de-ionized water were provided ad-libitum during the entire treatment period (90 days). Food consumption and body weight were recorded weekly (described in Table 14). For dynamic histomorphometric analysis fluorochrom dye Calcein (20 mg/kg body mass; Sigma-Aldrich, Israel) was IP injected to all rats at days 76 and 86. On day 90, rats were individually housed in metabolic cages and deprived from food and water for 18 h. Urine was collected from each metabolic funnel and was stored at −80° C. for future analysis of bone resorption biochemical marker at end of the experiment (Time 90). Immediately after urine sampling, serum samples were extracted for evaluation of formation biochemical marker of day 90. All rats were sacrificed by $CO_2$. Right femurs and 4$^{th}$ lumbar vertebras were dissected, wrapped with gaze pads soaked with saline buffer and kept in −80° C. for measurement of bone micro-CT scan. The 5$^{th}$ lumbar vertebras were stored in the same conditions as the right femurs for mechanical testing. Right tibias were dissected and placed immediately for 24 h at 4° C. in 3.7% formaldehyde solution (F1636, Sigma-Aldrich, Israel) for structural and dynamic histomorphometric measurements.

Micro-computed Tomography (μCT) Scanning

Trabecular and cortical bone microarchitecture of right femurs and 4$^{th}$ lumbar vertebras were analyzed in a μCT scanner (Skyscan 1174, Kartuizersweg Kontich, Belgium). Calibration of the scanner for bone mineral density (BMD) was performed according to manufacture instructions using a designated rat phantom rod with densities of 0.25 and 0.75 g/cm$^3$ (Skyscan, Kartuizersweg Kontich, Belgium).

Prior to scan analysis, femurs and 4$^{th}$ lumbar vertebras were removed from −80° C. and placed in a plastic (according to the manufacture guidance). The distal region of each femur was scanned for trabecular and cortical bone parameters at an isotropic resolution of 13.8 μm. Reconstruction was carried out employing a modified algorithm using the Skyscan Nrecon software (ver. 1.6.4, Skyscan). Volume of interest (VOI) was set to 0.8 mm below growth plate, and extended distally for 1.5 mm. Trabecular and cortical segments within the VOI were extracted by depicting ellipsoid contours every ~5 slices using the CT analysis software provided with the scanner (ver. 1.11 Skyscan). Trabecular and cortical BMD, bone volume (BV/TV, %), trabecular number (Tb.N), trabecular thickness (Tb.Th, μm), trabecular separation (Tb.Sp, μm) along with the micro-architectural parameters of trabecular bone pattern factor (TBPf) and structure model index (SMI) were calculated automatically by the CT analyzer software (ver. 1.11 Skyscan).

The 4$^{th}$ lumbar vertebra from each rat was scanned in a 13.8 μm isotropic resolution and VOI was set to cover 1.25 mm thick cross section from the center of the vertebral body for evaluation of the trabecular and cortical parameters in the same procedure as described above for the femurs.

Trial 6: Increasing Bone Mineral Density in Metabolic Bone Related Disorders

The inventors have conducted a study aiming to evaluate the effects of Amorphous Calcium Carbonate (ACC) on bone mineral density and bone fraction in metabolic bone disorders, and specifically osteoporosis as presented in the ovariectomized (OVX) rat model wherein the ACC is administered in combination with a standard medication for osteoporosis. In the present trial, five groups of rats were tested (4 OVX and 1 sham). Following operation, all rats were left untreated (fed with standard laboratory diet) to develop osteopenia for a period of 2 months. At the end of the induction period, the animals were treated with special food mixtures in the form of pellets from two different calcium sources: amorphous calcium carbonate (ACC) or crystalline calcium carbonate (CCC) (Table 16). Pellets from the two mixtures contained ~1% elemental calcium as confirmed by atomic absorption apparatus (Varian AA240, Palo Alto, Calif., USA) with no added vitamin D, except for the amounts found in the original food pellets (22 IU vitamin D/g). In addition, the animals were i.v injected (3 times/week) with either saline or 2 μg/kg alendronate (ALN) according to their group assignment, as described in Table 16.

TABLE 16

Assignment of rats according to the treatment

| Group | | Treatment |
|---|---|---|
| Sham | Sham | Low calcium diet (TDK95027, Harlan Inc.) containing 1% elemental calcium from CCC (Socal ® Precipitated Calcium Carbonate) ad libitum and subcutaneous injection of saline (0.9% NaCl, 100 μl/100 g b.w) 3 times\week. |
| OVX | CCC | Low calcium diet (TDK95027, Harlan Inc.) containing 1% elemental calcium from CCC (Socal ® Precipitated Calcium Carbonate), ad libitum and subcutaneous injection of saline (0.9% NaCl, 100 μl/100 g b.w) 3 times\week. |
| | ACC | Low calcium diet (TDK95027, Harlan Inc.) containing 1% elemental calcium from synthetic amorphous calcium carbonate [ACC (1% PS & 2% Citrate) provided by Mr. Oren Meiron, Amorphical] ad libitum and subcutaneous injection of saline (0.9% NaCl, 100 μl/100 g b.w) 3 times\week. |
| | CCC + ALN | Low calcium diet (TDK95027, Harlan Inc.) containing 1% elemental calcium from CCC (Socal ® Precipitated Calcium Carbonate) ad libitum and subcutaneous injection of alendronate (2 μg/kg as 100 μl/100 g b.w) 3 times\week. |
| | ACC + ALN | Low calcium diet (TDK95027, Harlan Inc.) containing 1% elemental calcium from synthetic amorphous calcium carbonate [ACC (1% PS & 2% Citrate) provided by Mr. Oren Meiron, Amorphical] ad libitum, and subcutaneous injection of alendronate (2 μg/kg as 100 μl/100 g b.w) 3 times\week. |

OVX = ovariectomy; CCC = crystalline calcium carbonate; ACC = amorphous calcium carbonate; ALN = alendronate; PS = phosphoserine Table 17 presents the mean food consumption and body weight of the rats during the trial. A significant weight increase was observed in all OVX rats compared to sham. This is despite the fact that food consumption was similar among all groups.

TABLE 17

Mean food consumption and total body weight of the rats

| | | OVX | | | |
|---|---|---|---|---|---|
| | Sham | CCC | ACC | CCC + ALN | ACC + ALN |
| Rat body weight (Day 0) | 258 (16) | 244 (18) | 240 (21) | 243 (14) | 244 (16) |
| Rat body weight (Day 60) | 289 (14) | 326 (19) | 323 (26) | 325 (15) | 327 (17) |
| Rat body weight (Day 180) | 319 (18) | 359 (23) | 360 (36) | 353 (18) | 355 (29) |
| Weight gain (%) | 24.5$^a$ | 47.5$^b$ | 50.3$^b$ | 46$^b$ | 45.4$^b$ |

TABLE 17-continued

Mean food consumption and total body weight of the rats

|  | Sham | OVX | | | |
|---|---|---|---|---|---|
|  |  | CCC | ACC | CCC + ALN | ACC + ALN |
| Mean food consumption (g/day) | 12.7 (0.73) | 12.9 (0.34) | 12.7 (0.82) | 12.7 (0.72) | 13.3 (1.4) |

Values were recorded weekly. Weight gain represents the increased rate of weigh from the beginning to the end of the experiment. Values are represented as mean (SD). One-way ANOVA: $p < 0.05$.
Letters represents Fisher-LSD post hoc comparison tests.

A micro-CT (μCT) three-dimensional schematic microarchitecture reconstruction of a representative distal femur and 4th vertebra from each group is presented in FIG. 5. The reconstruction of the femoral trabecular metaphysis as well as the vertebral body enables differentiation of three distinct groups: the first group comprising the Sham with the highest observed trabecular bone region (FIG. 5A), the second group comprising the OVX-CCC with the lowest trabecular bone region (FIG. 5B) in comparison to all other groups, a third group comprising OVX-ACC and OVX-CCC+ALN with a modest increase in trabecular bone region in comparison to the CCC (FIGS. 5C and 5D) and a fourth group comprising OVX-ACC+ALN with an additive increase in trabecular bone region compared to the third group (FIG. 5E).

The differences between the four groups observed are also reflected in the trabecular bone mineral density (BMD) and in the morphometric analysis of the femur metaphysis and $4^{th}$ lumbar vertebra presented in FIG. 6 and Table 18.

As illustrated in FIG. 6A-B, the trabecular femoral BMD of the Sham group was significantly higher compared to all four OVX groups. Within the OVX groups, the trabecular femoral and vertebral BMD of the ACC treated group (FIGS. 6A-B) were higher in comparison to the trabecular BMD of the CCC by 22% and 39%, respectively. The trabecular femoral and vertebral BMD of the CCC+ALN treated group were higher in comparison to the trabecular BMD of the CCC by 49% and 72%, respectively. The trabecular femoral and vertebral BMD of the ACC+ALN treated group were higher in comparison to the trabecular BMD of the CCC by 75% and 105%, respectively, and the addition of ACC to ALN instead of CCC increased the BMD by 26% and 33% in the femur and vertebra respectively, representing an additive positive effect on BMD values for ACC in combination with ALN.

In contrast to the trabecular BMD, no differences between all groups were observed in the cortical bone BMD (Ct. BMD) of both the femur and vertebra (Table 18).

TABLE 18

Morphometric microarchitectural analysis obtained by μCT scanning

|  |  | Sham | OVX | | | |
|---|---|---|---|---|---|---|
|  |  |  | CCC | ACC | CCC + ALN | ACC + ALN |
| (A) Femur | Tb. N, mm$^{-1}$ | 4.1 (0.7) | 1.5 (0.3) | 1.7 (0.1) | 2.3 (0.3) | 2.5 (0.3) |
|  | Tb. Sp, μm | 167 (41) | 682 (93) | 584 (95) | 360 (64) | 323 (47) |
|  | Tb. Th, μm | 111 (9) | 110 (10) | 112 (7) | 102 (11) | 105 (7) |
|  | Ct. BMD, g/cm$^3$ | 750 (32) | 756 (30) | 750 (67) | 741 (58) | 771 (27) |
|  | TBPf, mm$^{-1}$ | −7.0 (6.4) | 7.6 (1.7) | 6.1 (1.0) | 7.3 (1.8) | 6.3 (1.2) |
|  | SMI | 0.12 (0.2) | 1.66 (0.2) | 1.50 (0.1) | 1.63 (0.2) | 1.55 (0.1) |
| (B) Vertebra | Tb. N, mm$^{-1}$ | 3.60 (0.7) | 1.75 (0.5) | 2.05 (0.7) | 2.54 (0.3) | 2.73 (0.3) |
|  | Tb. Sp, μm | 199 (38) | 374 (87) | 352 (101) | 268 (42) | 251 (37) |
|  | Tb. Th, μm | 110 (17) | 98.4 (5.3) | 107 (13) | 100 (11) | 109 (13) |
|  | Ct. BMD, g/cm$^3$ | 750 (32) | 756 (30) | 750 (67) | 741 (58) | 771 (27) |
|  | TBPf, mm$^{-1}$ | −0.7 (5.8) | 8.5 (3.2) | 6.8 (2.3) | 4.8 (1.8) | 4.4 (1.9) |
|  | SMI | 0.61 (0.8) | 1.62 (0.3) | 1.56 (0.2) | 1.28 (0.2) | 1.22 (0.3) |

(A) Distal femurs metaphysis.
(B) $4^{th}$ lumbar vertebras.
Tb. N represents number of trabeculas within mm$^{-1}$ area, Tb. Sp represents the mean distance between trabeculas, Tb. Th represents mean thickness of the trabeculas, TBPf represents trabecular bone pattern factor and SMI represents structural model index.
Values are represented as mean (SD).

Morphometric analysis of the distal femur metaphysis and $4^{th}$ vertebral body exhibited a significant decrease in the trabecular bone fraction (BV/TV) in all ovariectomized groups in comparison to the Sham. Within the femurs and the vertebras of the OVX groups, ACC presented a significantly higher trabecular bone fraction in comparison to the CCC group by 34% and 23%, respectively. Similar results were also obtained for CCC+ALN group, which presented an increase of 37% in the femur and 46% in the vertebra in comparison to CCC. ACC in combination with ALN resulted in an increase of 56% in the femur and 71% in the vertebra in comparison to CCC, and in an increase of 19% and 25% in the femur and vertebra, respectively, in comparison to ALN+CCC group, again representing an additive effect on increase in BV/TV values for ACC in combination with ALN (FIG. 6C-D).

A significant decrease in the trabecular number (Tb.N) in all ovariectomized groups in comparison to the Sham was also observed in both the femur and vertebra. Within the femurs and vertebras of the OVX groups, ACC presented a higher trabecular number in comparison to the CCC group by an average of 17%. Higher results were obtained for CCC+ALN group, which presented an increase of 50% on average, in the femur vertebra in comparison to CCC. ACC in combination with ALN resulted in an average increase of 62% in the femur and vertebra in comparison to CCC, and in an average increase of 13% in the femur and vertebra, in comparison to ALN+CCC group, representing an additive effect on increase in Tb.N values for ACC in combination with ALN (Table 18).

A significant increase in the trabecular separation (Tb.Sp) in all ovariectomized groups in comparison to the Sham was observed in both the femur and vertebra. Within the femurs and vertebras of the OVX groups, ACC presented lower separation number in comparison to the CCC group by an average of 11%. Lower results were obtained for CCC+ALN group, which presented a decrease of 38% on average, in the femur and vertebra in comparison to CCC. ACC in combination with ALN resulted in a similar decrease of 54% in the femur and vertebra in comparison to CCC, and in an averaged decrease of 16% in the femur and vertebra, in comparison to ALN+CCC group, further supporting the additive effect of ACC in combination with ALN (Table 18).

Analysis of the trabecular thickness (Tb.Th) reveled no changes among all study groups in the femur, and only slight changes in the vertebra, manifested by an increase of only 12% in trabecular thickness in the Sham group compared to CCC, an increase of 9% in the ACC group compared to CCC group, only 2% increase following ALN treatment in comparison to CCC alone and a small additive effect of ACC in combination with ALN reflected by an increase of 11% in Tb.Th values, similar to the Sham group (Table 18). Microarchitectural analysis of topology and orientation parameters: trabecular bone pattern factor (TBPf) and structural model index (SMI) revealed that ovariectomy intervention resulted in an increase in TBPf and SMI values in both femur and vertebra. In the femur ACC treatment resulted in a greater decrease in TBPf and SMI values than CCC+ALN which had only a slight effect on these parameters in this region. Yet, in the vertebra, ACC treatment resulted in a smaller decrease in TBPf and SMI values compared to CCC+ALN. ACC+ALN treatment resulted in an additive averaged decrease of 12% in the femur and 37% in the vertebra for TBPf and SMI values in comparison to CCC treatment (Table 18).

Experimental Details

Animals

Fifty three 16 weeks old female Sprague Dawley rats (Harlan Inc., Jerusalem, Israel) with an average body weight of 246±17 g were group-housed in 26 cages (2-3 rats/cage) and acclimated under controlled room conditions (21±2° C. and 12-hours dark-light cycle). During 7 days acclimation, rats were fed with standard laboratory diet containing 1% elemental calcium (#2018SC Rat chow, Harlan Inc. Jerusalem, Israel) and de-ionized water ad-libitum.

For the administration of the different calcium sources, special food pellets were prepared. Low calcium rodent pellets containing 0.02% calcium (Rat chow #TD95027 Harlan Inc., Jerusalem, Israel) was finely grounded and separately mixed with two different calcium sources. A CCC mix containing 1% elemental calcium from crystalline calcium carbonate (Socal® Precipitated Calcium Carbonate), and an ACC mix containing 1% elemental calcium from stable amorphous calcium carbonate (containing 1% phosphoserine and 2% Citrate; Amorphical Ltd., Beer-Sheva, Israel). Every mix was separately pelleted and kept in a sealed bag at room temperature.

Following the 7 days acclimation period, rats were anesthetized by intraperitoneal (IP) injection of anesthetic solution (0.1 ml/100 g) containing Ketamine (Fort Dodge AH Ltd. Overland Park, USA) and Xylazine (EuroVet AH Ltd. Bladel, UK).

Rats were randomly assigned and operated according to their assigned five groups: Sham (sham-ovariectomized; n=9), and four other groups were ovariectomized (OVX) by a bilateral dorsal approach according to Lasota and Danowska-Klonowska (2004) Rocz Akad Med Bialymst 49 Suppl 1:129-131, and divided to OVX-CCC (n=10), OVX-ACC (n=10), OVX-CCC+ALN (n=12) and OVX-ACC+ALN (n=12). Following operation, rats were provided a 3 days recovery period through which they were treated with de-ionized water containing 1.5 ml/400 ml Dipyrone (Vitamed Ltd, Binyamina, Israel), and 1 mg/kg Enrofloxacin (Buyer Ltd. Leverkusen, Germany). The animals were left untreated under the same conditions as the acclimation period, standard laboratory diet ad-libitum for 2 months to develop Osteopenia.

Following 2 months, rats started treatment according to their assignment as described in Table 16 for a period of 4 months. The assigned supplemental pellets and de-ionized water were provided ad-libitum during the entire treatment period. Food consumption and body weight were recorded weekly (Table 17). At the end of the treatment period, all rats were sacrificed by $CO_2$. Right femurs and $4^{th}$ lumbar vertebras were dissected, wrapped with gaze pads soaked with saline buffer and kept in −80° C. for measurement of bone micro-CT scan.

Micro-computed Tomography (µCT) Scanning

Trabecular and cortical bone microarchitecture of right femurs and $4^{th}$ lumbar vertebras were analyzed in a µCT scanner (Skyscan 1174, Kartuizersweg Kontich, Belgium). Calibration of the scanner for bone mineral density (BMD) was performed according to manufacture instructions using a designated rat phantom rod with densities of 0.25 and 0.75 g/cm$^3$ (Skyscan, Kartuizersweg Kontich, Belgium).

Prior to scan analysis, femurs and $4^{th}$ lumbar vertebras were removed from −80° C. and placed in a plastic (according to the manufacture guidance). The distal region of each femur was scanned for trabecular and cortical bone parameters at an isotropic resolution of 13.8 µm. Reconstruction was carried out employing a modified algorithm using the Skyscan Nrecon software (ver. 1.6.4, Skyscan). Volume of interest (VOI) was set to 0.8 mm below growth plate, and extended distally for 1.5 mm. Trabecular and cortical segments within the VOI were extracted by depicting ellipsoid contours every ~5 slices using the CTan analysis software provided with the scanner (ver. 1.11 Skyscan). Trabecular and cortical BMD, bone volume (BV/TV, %), trabecular number (Tb.N), trabecular thickness (Tb.Th, µm), trabecular separation (Tb.Sp, µm) along with the micro-architectural parameters of trabecular bone pattern factor (TBPf) and structure model index (SMI) were calculated automatically by the CT analyzer software (ver. 1.11 Skyscan).

The $4^{th}$ lumbar vertebra from each rat was scanned in a 13.8 µm isotropic resolution and VOI was set to cover 1.25 mm thick cross section from the center of the vertebral body for evaluation of the trabecular and cortical parameters in the same procedure as described above for the femurs.

The results of the above trial confirmed that stable ACC has higher effect on bone mineral density and other bone parameters that CCC. Moreover, the administration of ACC in combination with standard medication for treatment of bone loss resulted in additive effect compared to CCC, allowing the decrease of bisphosphonate dosage and confirming that highly bioavailable ACC can be used for increasing bone mineral density and treating metabolic bone disorders, diseases and conditions alone or together with the conservative medications.

Trial 7: Preventing or Delaying the Onset of Metabolic Bone Disorders

The inventors have conducted a study aiming to evaluate the effect calcium from stable Amorphous Calcium Carbonate (ACC) compared to crystalline calcium carbonate (CCC), on the prevention of bone metabolic disorders and specifically osteoporosis as presented in the ovariectomized (OVX) rat model.

In the study, five groups of rats were tested (4 ovariectomized and 1 sham). The OVX animals were fed with special food mixtures in the form of pellets from four different calcium sources: commercial crystalline calcium carbonate served as control (mix A), natural ACC (Gastrolith powder) (mix B), synthetic ACC (comprising trace amounts of phospho-serine) (mix C), and commercial crystalline calcium citrate (mix D). Sham group was administrated with the same food as the control. Pellets from all four mixtures contained ~0.5% elemental calcium as confirmed by atomic absorption apparatus (Varian AA240, Palo Alto, Calif., USA) and described in Table 19 with no added vitamin D, except for the amounts found in the original food pellets (22 IU vitamin D/g).

TABLE 19

Elemental calcium content (% in weight) of the calcium source and specialized pellets as was measured by atomic absorption

|  | Carbonate (Mix A) | Gastrolith (Mix B) | ACC (Mix C) | Citrate (Mix D) |
| --- | --- | --- | --- | --- |
| % $Ca^{2+}$ in the calcium source | 34.54 | 28.1 | 33.0 | 18.3 |
| % $Ca^{2+}$ in the pellets | 0.54 | 0.54 | 0.53 | 0.55 |

The source of the calcium was obtained from: commercial crystalline $CaCO_3$ (Carbonate), gastrolith powder from the Australian crayfish *Cherax quadricarinatus* (Gastrolith), synthetic stable amorphous calcium carbonate (ACC) and calcium citrate from a commercial supplement (Citrate). Values are represented as mean.

Table 20 presents the mean food consumption and body weight of the rats during the trial. A significant weight increase was observed in all OVX rats compared to sham. This is despite the fact that food consumption was similar among all groups.

A μCT three-dimensional schematic microarchitecture reconstruction of a representative distal femur and 4th vertebra from each group is presented in FIG. 7. The reconstruction of the femoral trabecular metaphysis as well as the vertebral body enables differentiation of three distinct groups: the first group comprising the Sham with the highest observed trabecular bone region (FIG. 7A), the second group comprising the OVX Control and Citrate with the lowest trabecular bone region (FIGS. 7B and 7E) in comparison to the Sham, and a third group comprising OVX Gast and ACC with a modest decrease in trabecular bone region in comparison to the Sham (FIGS. 7C and 7D).

The differences between the three groups observed are also reflected in the trabecular bone mineral density (BMD) and in the morphometric analysis of the femur metaphysis and $4^{th}$ lumbar vertebra presented in FIG. 8, FIG. 9 and Table 21.

As illustrated in FIG. 8A, the trabecular femoral BMD of the Sham group was significantly higher compared to all four OVX groups: the Control, Gast, ACC and Citrate with significant differences of 64%, 45%, 50% and 63%, respectively. Comparable values were also obtained in the trabecular vertebral BMD, presented in FIG. 8B, of the Sham group compared to all four OVX groups. Within the OVX groups, the trabecular femoral and vertebral BMD of Gast and ACC (FIGS. 8A and 8B) were significantly higher in comparison to the trabecular BMD of the Control by 56% and 38% in the femur and 38% and 32% in the vertebra, respectively. No significant differences were observed in the trabecular femoral and vertebral BMD of the Citrate in comparison to the Control. Comparison between the Gast and ACC groups revealed statistical differences of 13% in favor of Gast over the ACC in the trabecular femoral BMD and no difference in the trabecular vertebral BMD.

In contrast to the trabecular BMD, no significant differences between all groups were observed in the cortical bone BMD (Ct. BMD) of both the femur and vertebra (Table 21).

TABLE 20

Mean food consumption and total body weight of the rats at the beginning and at the end of the experiment

|  | Sham | OVX | | | |
| --- | --- | --- | --- | --- | --- |
|  |  | Control | Gastrolith | ACC | Citrate |
| Rat body weight (Day 0) | 253 (3.5) | 249 (3.3) | 249 (5.2) | 251 (4) | 253 (4.7) |
| Rat body weight (Day 90) | 310 (8.3) | 345 (5.8) | 370 (6.4) | 359 (4.2) | 354 (5.6) |
| Weight gain (%) | 22.5[a] | 38.5[b] | 48.5[b] | 43[b] | 40[b] |
| Mean food consumption | 15.2 (0.07) | 15.2 (0.07) | 15.2 (0.07) | 15.1 (0.02) | 15.2 (0.05) |

Values were recorded weekly. Weight gain represents the increased rate of weigh from the beginning to the end of the experiment. Values are represented as mean (SD). One-way ANOVA: $p < 0.05$.
Letters represents Fisher-LSD post hoc comparison tests.

TABLE 21

Morphometric analysis and cortical bone mineral density (Ct. BMD) obtained by μCT scanning

| | | Sham | OVX | | | |
| --- | --- | --- | --- | --- | --- | --- |
| | | | Control | Gastrolith | ACC | Citrate |
| (A) Femur | **Tb. N, mm$^{-1}$ | 6.1$^a$ (0.9) | 2.2$^b$ (0.6) | 3.5$^c$ (0.6) | 3.3$^c$ (0.5) | 2.4$^b$ (0.5) |
| | **Tb. Sp, μm | 111$^a$ (28) | 248$^b$ (83) | 158$^c$ (46) | 209$^d$ (74) | 226$^{bd}$ (47) |
| | *Tb. Th, μm | 31.5$^{ac}$ (5.3) | 29.0$^b$ (0.8) | 33.6$^a$ (3.5) | 30.9$^{cb}$ (1.4) | 29.1$^b$ (2.0) |
| | Ct. BMD, g/cm$^3$ | 963 (51) | 980 (57) | 983 (62) | 952 (53) | 970 (53) |
| (B) Vertebra | **Tb. N, mm$^{-1}$ | 3.98$^a$ (0.67) | 1.57$^b$ (0.33) | 2.29$^c$ (0.25) | 2.24$^c$ (0.34) | 1.59$^b$ (0.22) |
| | **Tb. Sp, μm | 153$^a$ (28) | 254$^b$ (74) | 197$^c$ (54) | 229$^{bc}$ (36) | 262$^b$ (60) |
| | Tb. Th, μm | 84.6 (7.3) | 87.5 (6.4) | 83.8 (20.3) | 93.5 (6.9) | 86.6 (8.5) |
| | Ct. BMD, g/cm$^3$ | 933 (55) | 950 (50) | 959 (56) | 961 (57) | 943 (68) |

(A) Distal femurs metaphysis.
(B) 4$^{th}$ lumbar vertebras.
Tb. N represents number of trabeculas within mm$^{-1}$ area, Tb. Sp represents the mean distance between trabeculas, Tb. Th represents mean thickness of the trabeculas.
One-way ANOVA:
*$p < 0.05$,
**$p < 0.01$.
Letters represents Fisher-LSD post hoc comparison tests.

Morphometric analysis of the distal femur metaphysis and 4$^{th}$ vertebral body (FIG. 9 and Table 21) exhibited a significant decrease in the trabecular bone fraction (BV/TV) and its number (Tb.N) in all ovariectomized groups in comparison to the Sham. The Control group was significantly lower by 65% on average in the distal femur (FIG. 9A and Table 21A) and by 60% in the vertebra (FIG. 3B and Table 3B) in comparison to the Sham. Whereas the average of the OVX Gast and ACC groups in the distal femur was lower by only 41% and 49% in comparison to the Sham, and lower in 40% and 41% in the vertebra, respectively. Within the femurs of the OVX groups, Gast and ACC presented a significantly higher trabecular bone fraction and trabecular number in comparison to the Control by an average of 65% and 49%, respectively. Similar results were also obtained in the lumbar vertebra of the Gast and ACC groups with a higher average of 48% and 47% in comparison to Control, respectively. No significant differences were observed in the trabecular bone fraction and its number between the Citrate and the Control.

Comparison between the femurs of Gast and ACC groups revealed a significant difference in bone fraction, trabecular thickness and trabecular separation. According to the results presented in FIG. 9A and Table 21A, the femurs of Gast group exhibited a significant higher bone fraction of 16%, a higher trabecular thickness of 9% and a lower trabecular separation of 24% in comparison to ACC. A significantly higher trabecular thickness of 12% was also observed in the vertebra of Gast in comparison to ACC but no significant differences were observed in the rest of the morphometric parameters between Gast and ACC (FIG. 9B and Table 21B).

The differences between the groups in the microarchitecture structure are further emphasized in the un-decalcified structural histomorphometric analysis of the proximal tibia, presented in Table 22A. According to the results presented in Table 22A, all OVX groups, namely the Control, Gast, ACC and Citrate presented significantly lower trabecular bone fraction and condensed trabeculas values compared to the Sham (with an average of 55%, 19%, 32% and 55%, respectively). Moreover, the trabecular separation was significantly higher in all OVX groups in comparison to Sham (Table 22A) by 130% for the Control, 30% for Gast, 60% for ACC and 148% for Citrate. Within the OVX groups, Gast and ACC presented a significantly higher trabecular bone fraction and trabecular number with an average of 80% and 50%, and a lower trabecular separation of 44% and 31%, in comparison to Control, respectively. The Citrate group presented a higher significant trabecular thickness of 13% compared to Control. Comparison of structural histomorphometric parameters between Gast and ACC groups revealed a significant difference in bone fraction, trabecular number and trabecular separation. According to Table 22A, Gast group presented higher bone fraction and trabecular number of 19% and 21%, in comparison to ACC and a lower trabecular separation value of 20% in comparison to ACC, respectively.

TABLE 22

Histomorphometric analysis of un-decalcified sections from the proximal tibias

| | | Sham | OVX | | | |
| --- | --- | --- | --- | --- | --- | --- |
| | | | Control | Gastrolith | ACC | Citrate |
| (A) Structural | **BV/TV, % | 28.5$^a$ (4.1) | 12.8$^b$ (2.1) | 23$^c$ (3.3) | 19.4$^d$ (2.8) | 12.8$^b$ (1.4) |
| | **Tb. N, mm$^{-1}$ | 5.6$^a$ (0.6) | 2.5$^b$ (0.5) | 4.5$^c$ (0.4) | 3.7$^d$ (0.8) | 2.3$^b$ (0.3) |
| | **Tb. Sp, μm | 128$^a$ (25) | 296$^b$ (44) | 166$^c$ (15) | 205$^d$ (43) | 318$^b$ (42) |
| | *Tb. Th, μm | 51.2$^{ab}$ (6.2) | 47.1$^a$ (6.0) | 51.6$^{ab}$ (7.1) | 54.8$^b$ (7.7) | 53$^b$ (9.9) |

TABLE 22-continued

Histomorphometric analysis of un-decalcified sections from the proximal tibias

| | | | OVX | | | |
|---|---|---|---|---|---|---|
| | | Sham | Control | Gastrolith | ACC | Citrate |
| (B) Dynamic | **BFR/BS, μm²/μm/day | 0.145$^a$ (0.026) | 0.164$^a$ (0.021) | 0.214$^b$ (0.025) | 0.206$^b$ (0.027) | 0.159$^a$ (0.019) |
| | **MS/BS, % | 8.04$^a$ (1.53) | 8.31$^a$ (1.42) | 11.61$^b$ (1.36) | 11.09$^b$ (1.18) | 8.25$^a$ (1.44) |
| | MAR, μm/day | 1.26 (0.26) | 1.30 (0.19) | 1.34 (0.25) | 1.29 (0.21) | 1.40 (0.20) |

(A) Structural parameters were analyzed from 4 μm stained sections (MacNeal).
(B) Dynamic parameters were analyzed from un-decalcified sections double-labeled with calcein fluorescent dye.
All values were calculated using the BIOQUANT Image software analysis (Bioquant OSTEO, ver. 7.20.10).
One-way ANOVA:
*p < 0.05,
**p < 0.01,
Letters represents Fisher-LSD post hoc comparison tests.

The results of the dynamic histomorphometry analysis are presented in Table 22B. According to the results, no significant differences were observed in the bone formation rate to bone surface (BFR/BS) and mineralizing surface to bone surface (MS/BS) of the OVX Control and Citrate groups in comparison to Sham. On the other hand, bone formation rate of the OVX Gast and ACC were 53% and 50% higher, in comparison to Sham, and MS/BS of the OVX Gast and ACC presented similar elevations of 44% and 38%, respectively compared to the sham. Within the OVX groups, Gast and ACC presented a significant higher bone formation rate of 38% and 35%, and significant higher MS/BS of 40% and 33%, in comparison to Control, respectively. The OVX Citrate group presented no significant difference from to the Control but a statistical lower bone formation rate of 28% from Gast and 26% from ACC. MS/BS of the OVX Citrate group was similar to that of the Control and significantly lower by 29% and 26% from the Gast and ACC groups, respectively.

Mineral apposition rate (MAR) revealed no significant differences in all OVX groups compared to Sham, and no differences of the OVX Gast, ACC and Citrate in comparison to Control. EIA kit assessment of bone turnover by serum osteocalcin (OC) formation marker and urine deoxypyridinoline (DPD) resorption marker of each group at the end of the experiment (day 90) are presented in Table 23. Both markers were evaluated for baseline prior to randomization (at day 0, data not shown).

from the ACC (32%) groups. DPD levels from Gast were not statistically lower than the Citrate but presented a difference of 31%. In the serum OC marker, no significant changes were observed between any of the groups.

The results from the mechanical strength analysis of the 5$^{th}$ lumbar vertebra are presented in FIG. 10. According to the results, the mechanical strength properties of the OVX Control, Gast and Citrate were significantly lower in comparison to Sham by an average of 41%, 40% and 40%, respectively. Whereas, the mechanical strength values of the ACC group were significantly lower by an average of 17% in comparison to the Sham. These differences were statistically significant in most parameters evaluated, except for the ultimate force parameter which was not statistically different (FIG. 10D). Within the OVX groups, ACC group presented significantly higher values in comparison to the Control in every tested parameter: ultimate force (FIG. 10A), energy to ultimate force (FIG. 10B), toughness (FIG. 10C) and energy to yield (FIG. 10D) by an average of 37%, 49%, 29% and 65%, respectively. These differences are also reflected in the in the higher values of OVX ACC in comparison to the Gast and Citrate groups with an average of 42% and 37%, respectively. The OVX Gast and Citrate groups did not present any statistical difference to the Control or between them in any of the mechanical strength parameters tested.

Micro-CT analysis of the 4$^{th}$-lumbar vertebra showed that the trabecular bone pattern factor (TBPf) is far lower (91% on average) in the sham group than in the OVX-control,

TABLE 23

Assessment of serum osteocalcin (OC) formation marker and urine deoxypyridinoline (DPD) resorption marker for each group at day 90

| | | OVX | | | |
|---|---|---|---|---|---|
| | Sham | Control | Gastrolith | ACC | Citrate |
| *DPD (nmol/mmol Cr) | 13.75$^a$ (5.44) | 36.65$^{be}$ (31.16) | 29.823$^{bd}$ (16.56) | 22.59$^{ad}$ (11.09) | 43.55$^e$ (22.97) |
| OC (ng/ml) | 10.0$^a$ (4.8) | 14.8$^a$ (6.4) | 14.72$^a$ (8.7) | 12.7$^a$ (6.8) | 15.7$^a$ (8.4) |

One-way ANOVA:
*p < 0.05

At day 90, significant higher DPD levels were observed in all OVX groups compared to the Sham, except for the ACC group that presented a non-significant difference from the Sham, and a significant lower DPD level from the Control (39%), and Citrate (48%) groups. The Gast group presented lower level from the Control (19%) and higher DPD level OVX-gastrolith and OVX-citrate groups. The TBPf of the sham group was, however, lower (61%) than what was measured for the OVX-ACC group. Within the OVX groups, the TBPf of the OVX-ACC groups was significantly lower than that of the OVX-control, OVX-citrate and OVX-gastrolith groups by an average of 33% (FIG. 10E; p<0.001).

Structural model index (SMI) evaluation points to the same trend, being significantly lower in the sham group, compared to the OVX-control, OVX-gastrolith and OVX-citrate groups (43% on average). The SMI of the sham group was, however, lower (30%) than what was measured for the OVX-ACC group. Here, values obtained with the OVX-ACC group were significantly lower that what was measured for the OVX-control and OVX-citrate groups (14% on average). At the same time, SMI values obtained with the OVX-ACC group were reduced relative to the index measured with the OVX-gastrolith group (FIG. 10F; p<0.001). The last micro-architectural parameter measured, namely the degree of anisotropy (DA), was lower in the sham group, compared to the OVX-control, OVX-gastrolith and OVX-citrate groups, by 22% on average. No significant differences in DA was observed between the sham and OVX-ACC groups, or among all OVX groups, although OVX-ACC showed lower values that measured with the other OVX groups (FIG. 10G; p<0.001).

Experimental Details

Animals

One hundred and one 16-17 weeks old female Sprague Dawley rats (Harlan Inc., Jerusalem, Israel) with an average body weight of 250±16 g were group-housed in 33 cages (~3 rats/cage) and acclimated under controlled room conditions (21±2° C. and 12-hours dark-light cycle). During 7 days acclimation, rats were fed with standard laboratory diet containing 1% elemental calcium (#2018SC Rat chow, Harlan Inc. Jerusalem, Israel) and de-ionized water ad-libitum. Following the 7 days acclimation period, rats were housed individually in metabolic cages and deprived from food and water for 18 h. Urine was collected from each metabolic funnel and was stored at −80° C. for future analysis of bone resorption biochemical marker at baseline (time 0).

For the administration of the different calcium sources, special food pellets containing were prepared. Low calcium rodent pellets containing 0.02% calcium (Rat chow #TD95027 Harlan Inc., Jerusalem, Israel) was finely grounded and separately mixed with four different calcium sources. A control mix containing calcium carbonate from a commercial supplement (mix A), Gast mix containing gastrolith powder harvested from the Australian crayfish *Cherax quadricarinatus* (mix B) (Ben's farm, Beer Tzofar, Israel), ACC mix containing stable amorphous calcium carbonate and P-serine (P-Ser) (mix C) (Batch #ETS001, Amorphical Ltd., Beer-sheva, Israel) and the Citrate mix containing calcium citrate from a commercial supplement (mix D). Every mix was separately pelleted and kept in a sealed bag at room temperature.

Immediately after urine sampling, rats were anesthetized using intraperitoneal (IP) injection of anesthetic solution (0.1 ml/100 g) containing Ketamine (Fort Dodge AH Ltd. Overland Park, USA) and Xylazine (EuroVet AH Ltd. Bladel, UK). Blood was sampled from rat's tail (approximately 180 μl) and centrifuged for 10 minutes at 3000 g using a tabletop centrifuge (Hettich Zentrifugen, Bach, Switzerland) for serum extraction. Serum samples were stored at −80° C. for future analysis of bone formation biochemical marker at baseline (Time 0).

Rats were randomly assigned and operated according to their assigned five groups: Sham (sham-Ovariectomized) fed with mix A, and four other groups were ovariectomized (OVX) using a bilateral dorsal approach according to Lasota and Danowska-Klonowska (2004) Rocz Akad Med Bialymst 49 Suppl 1:129-131, and divided to OVX Control (fed with mix A), OVX Gast (fed with mix B), OVX ACC (fed with mix C) and OVX Citrate (fed with mix D). Following operation, rats were provided a 7 days recovery period under the same conditions as the acclimation period, standard laboratory diet ad-libitum and de-ionized water containing 1.5 ml/400 ml Dipyrone (Vitamed Ltd, Binyamina, Israel), and 1 mg/kg Enrofloxacin (Buyer Ltd. Leverkusen, Germany).

Experimental Treatment

At the end of the recovery period the rats were group-housed in 47 cages (2 rats/cage) according to the group assignment, under the same controlled room conditions as described above. The assigned supplemental pellets and de-ionized water were provided ad-libitum during the entire treatment period (90 days). Food consumption and body weight were recorded weekly (Table 2). For dynamic histomorphometric analysis fluorochrom dye Calcein (20 mg/kg body mass; Sigma-Aldrich, Israel) was IP injected to all rats at days 76 and 86. On day 90, rats were individually housed in metabolic cages and deprived from food and water for 18 h. Urine was collected from each metabolic funnel and was stored at −80° C. for future analysis of bone resorption biochemical marker at end of the experiment (Time 90). Immediately after urine sampling, serum samples were extracted for evaluation of formation biochemical marker of day 90 and stored in the same manner as described at day 0. All rats were sacrificed by $CO_2$. Right femurs and $4^{th}$ lumbar vertebras were dissected, wrapped with gaze pads soaked with saline buffer and kept in −80° C. for measurement of bone micro-CT scan. The $5^{th}$ lumbar vertebras were stored in the same conditions as the right femurs for mechanical testing. Right tibias were dissected and placed immediately for 24 h at 4° C. in 3.7% formaldehyde solution (F1636, Sigma-Aldrich, Israel) for structural and dynamic histomorphometric measurements.

Micro-computed Tomography (μCT) Scanning

Trabecular and cortical bone microarchitecture of right femurs and $4^{th}$ lumbar vertebras were analyzed using a μCT scanner (Skyscan 1174, Kartuizersweg Kontich, Belgium). Calibration of the scanner for bone mineral density (BMD) was performed according to manufacture instructions using a designated rat phantom rod with densities of 0.25 and 0.75 $g/cm^3$ (Skyscan, Kartuizersweg Kontich, Belgium).

Prior to scan analysis, femurs and $4^{th}$ lumbar vertebras were removed from −80° C., transferred to new gauze pads soaked with 70% ethanol and placed in a plastic vial filled with 70% ethanol (according to the manufacture guidance). The distal region of each femur was scanned for trabecular and cortical bone parameters at an isotropic resolution of 13.8 μm. Reconstruction was carried out employing a modified algorithm using the Skyscan Nrecon software (ver. 1.6.4, Skyscan). Volume of interest (VOI) was set to 0.5 mm below growth plate, and extended distally for 1.5 mm. Trabecular and cortical segments within the VOI were extracted by depicting ellipsoid contours every ~5 slices using the CTan analysis software provided with the scanner (ver. 1.11 Skyscan).

Trabecular and cortical BMD, bone volume (BV/TV, %), trabecular number (Tb.N), trabecular thickness (Tb.Th, μm), and trabecular separation (Tb.Sp, μm) were calculated automatically by the CTan analyzer software (ver. 1.11 Skyscan).

The $4^{th}$ lumbar vertebra from each rat was scanned in a 13.8 μm isotropic resolution and VOI was set to cover 2.0 mm thick cross section from the center of the vertebral body.

Trabecular and cortical bone parameters were evaluated in the vertebral body, set to cover a VOI of a 2-mm thick cross-section, starting 0.14 mm below the cranial growth plate. In addition to the same trabecular and cortical bone parameters as studied for the distal femur, the topology parameters: i.e, trabecular bone pattern factor (TBPf) and structural model index (SMI); and the trabecular orientation parameter, degree of anisotropy (DA) were also measured in the vertebral body.

Histomorphometry

Right tibias were removed from the formaldehyde solution and dehydrated through an ethanol gradient, cleared using xylene (24250521, Bio-Lab Ltd. Haifa, Israel), and infiltrated with 80% methylmethacrylate (MMA; M5599, Sigma Aldrich, Rehovot, Israel)+20% dibutyl phthalate (DBP; 61-5062, Merck Ltd, Hohenbrunn, Germany) for 3 days at 4° C. Specimens were then transferred to MMA+DBP+Benozoyl peroxide (617008, Merck Ltd, Hohenbrunn, Germany) solution for another 6 days infiltration at 4° C. Following infiltration procedure, specimens were embedded in MMA+DBP+2.5% Benozoyl peroxide under a temperature gradient (from 38° C. to 50° C. over a period of 4 days). Mid-sagittal (4 µm) un-decalcified sections from each specimen were cut using a Lecia RM 2025 microtome (Lecia Instruments Ltd, Petach Tikva, Israel) connected to tungsten carbide knifes (Disposable blade; TC65, Rhenium Inc. Bet-Nekufa, Israel). Most sections were stained with McNeal's tetrachrome for structural histomorphometry. The remaining sections were left unstained for dynamic histomorphometry.

Measurement of both structural and dynamic histomorphometry of the proximal tibia metaphisyes were obtained using a semi-automatic analysis system (Bioquant OSTEO, ver. 7.20.10, BIOQUANT Image Analysis Corporation Nashville, USA) which is connected to a microscope (Nikon Optiphot 2, Kingston, England) equipped with fluorescent light source.

Histomorphometric parameters such as bone volume (BV/TV, %), trabecular number (Tb.N), trabecular thickness (Tb.Th, µm), trabecular separation (Tb.Sp, µm), bone formation rate/bone sample (BFR/BS), mineralizing surface/bone surface (MS/BS) and mineral apposition rate (MAR) were calculated using the BIOQUANT Image software analysis (Bioquant OSTEO, ver. 7.20.10).

Evaluation of Bone Turnover Biochemical Markers

Serum Osteocalcin (OC) concentration was determined by EIA kit (#BT-490, Biomedical Technologies Inc. Stoughtone, USA) following a 1:10 serum dilution.

Urinary Deoxypyridinoline (DPD) concentration was determined by commercial EIA kit (#8007, Qudiel Inc. San Diego, USA) following a 1:50 dilution. DPD levels were normalized to Creatinine levels (#8009, Qudiel Inc. San Diego, USA).

Mechanical Strength of the $5^{th}$ Lumbar Vertebra

Mechanical properties (Ultimate force, Energy to ultimate force, Toughness and Energy to yield) were obtained from the compression tests of $5^{th}$ lumbar vertebral body (L5). Calculation of the material properties were performed by measuring the height of the vertebral body and the average of caudal and cranial diameters using a caliper. Cross sectional area (CSA) and bone volume (BV) were obtained by µCT scanning that covered the entire bone including both trabecular and cortical shell.

Statistical Analysis

Results are expressed herein as means±SEM. One-way ANOVA and Fisher-LSD post hoc comparison tests were performed using STATISTICA 6.1 software (StaSoft, Tulsa, Okla.). A p value <0.05 was deemed significant.

The results of the above trial confirmed that stable ACC has higher effect on bone mineral density and other bone parameters that CCC in study group susceptible to the development of osteoporosis. The superior bioavailability of ACC allows the use thereof for preventing or delaying the onset of metabolic bone disorders, diseases and conditions.

Although embodiments of the invention have been described by way of illustration, it will be understood that the invention may be carried out with many variations, modifications, and adaptations, without exceeding the scope of the claims.

The invention claimed is:

1. A method of treating calcium malabsorption associated with hypoparathyroidism in a subject suffering from a disorder of calcium metabolism associated with a decrease of plasma calcium concentration below 8.8 mg/dL, the method comprising:
   orally administering to said subject an effective amount of a composition comprising stable synthetic amorphous calcium carbonate (ACC) comprising at least one stabilizer, wherein the amount of the elemental calcium administered in said ACC is 50% or less of elemental calcium of a crystalline calcium carbonate standard dose, wherein the composition is present in an oral dosage form, and wherein each dosage form comprises at least 50 mg of elemental calcium.

2. The method according to claim 1, wherein said at least one stabilizer is selected from the group consisting of organic acids, phosphoric or sulfuric esters of hydroxy carboxylic acids, hydroxyl bearing organic compounds, phosphorylated amino acids, polyols, and combinations thereof.

3. The method according to claim 2, wherein said at least one stabilizer comprises at least one component selected from phosphoric esters of hydroxy carboxylic acids and hydroxyl bearing organic compounds.

4. The method according to claim 2, wherein said at least one stabilizer comprises at least one component selected from phosphorylated amino acids and polyols.

5. The method according to claim 2, wherein said at least one stabilizer comprises hydroxyl bearing organic compounds that are further combined with at least one alkali hydroxide.

6. The method according to claim 2, wherein said at least one stabilizer comprises a carboxylic acid.

7. The method according to claim 6, wherein the carboxylic acid is selected from the group consisting of citric acid, tartaric acid, malic acid, and combinations thereof.

8. The method according to claim 2, wherein said at least one stabilizer comprises at least one compound selected from the group consisting of phosphorylated amino acids, phosphorylated peptides, chitin together with at least one peptide, and polyol together with alkaline hydroxide.

9. The method according to claim 1, wherein said composition further comprises carriers, adjuvants, diluents, or excipients.

10. The method according to claim 1, wherein said subject is in a fasting state or in a fed state.

11. A method of treating calcium malabsorption associated with hypoparathyroidism in a subject in need thereof, the method comprising:
   orally administering to said subject an effective amount of a composition comprising stable amorphous calcium carbonate (ACC) comprising at least one stabilizer, wherein the dose of ACC is 50% or less of the effective crystalline calcium carbonate dose, wherein the composition is present in an oral dosage form, and wherein each dosage form comprises at least 50 mg of elemental calcium.

12. The method of claim 11, wherein said ACC is obtained from isolated crustacean gastrolith.

13. The method according to claim 11, wherein said composition includes carriers, adjuvants, diluents, or excipients.

14. A method of treating calcium malabsorption in a subject suffering from hypoparathyroidism, the method comprising:
   orally administering to said subject stable amorphous calcium carbonate (ACC) comprising at least one stabilizer;
   wherein an amount of elemental calcium administered in said ACC is 50% or less of elemental calcium in a crystalline calcium carbonate standard dose, wherein the composition is present in an oral dosage form, and wherein each dosage form comprises at least 50 mg of elemental calcium.

15. The method of any one of claims 1, 11 and 14, wherein the dosage form comprises from 50 mg to 1 g of elemental calcium.

16. The method of claim 15, wherein the dosage form comprises from 50 to 200 mg of elemental calcium.

17. The method of claim of claim 1, wherein the dosage form is selected from a tablet and a capsule.

18. The method of claim of claim 11, wherein the dosage form is selected from a tablet and a capsule.

19. The method of claim of claim 14, wherein the dosage form is selected from a tablet and a capsule.

* * * * *